(12) United States Patent
Wawrzonek et al.

(10) Patent No.: US 8,419,270 B2
(45) Date of Patent: Apr. 16, 2013

(54) SYSTEMS AND METHODS FOR PRODUCING THERMAL MECHANICAL FATIGUE ON GAS TURBINE ROTORS IN A SPIN TEST ENVIRONMENT

(75) Inventors: Paul Wawrzonek, Bondsville, MA (US); H. Eric Sonnichsen, Marlborough, MA (US); Robert L. Murner, Wilbraham, MA (US)

(73) Assignee: Test Devices, Inc., Hudson, MA (US)

( * ) Notice: Subject to any disclaimer, the term of this patent is extended or adjusted under 35 U.S.C. 154(b) by 470 days.

(21) Appl. No.: 12/489,023

(22) Filed: Jun. 22, 2009

(65) Prior Publication Data
US 2009/0316748 A1    Dec. 24, 2009

Related U.S. Application Data

(60) Provisional application No. 61/132,686, filed on Jun. 20, 2008.

(51) Int. Cl.
*G01N 3/00* (2006.01)
*G01K 1/00* (2006.01)
*G01K 3/00* (2006.01)

(52) U.S. Cl.
USPC .............. 374/46; 374/144; 374/137; 374/141

(58) Field of Classification Search ............ 374/46, 374/144, 137, 141
See application file for complete search history.

(56) References Cited

U.S. PATENT DOCUMENTS

| | | | | |
|---|---|---|---|---|
| 4,878,379 | A * | 11/1989 | Deer | 73/54.39 |
| 5,520,042 | A * | 5/1996 | Garritano et al. | 73/54.02 |
| 5,864,238 | A | 1/1999 | Iijima et al. | |
| 8,006,544 | B2 * | 8/2011 | Holmes et al. | 73/112.01 |
| 8,109,669 | B2 * | 2/2012 | Aderhold et al. | 374/124 |
| 2001/0019661 | A1 | 9/2001 | Choi | |
| 2001/0022802 | A1 * | 9/2001 | Kurata | 374/45 |
| 2003/0062304 | A1 | 4/2003 | Sueyoshi et al. | |
| 2007/0012092 | A1 | 1/2007 | Aubriat et al. | |

OTHER PUBLICATIONS

International Search Report for application No. PCT/US2009/048122, dated Aug. 20, 2009.
Written Opinion of the International Searching Authority for application No. PCT/US2009/048122, dated Aug. 20, 2009.

* cited by examiner

*Primary Examiner* — Mirellys Jagan
(74) *Attorney, Agent, or Firm* — Preti Flaherty Beliveau & Pachios LLP

(57) ABSTRACT

A test facility includes a heat source to thermally load a test object being mechanically loaded by rotation imposed by a spin test rig. The heat source can be a quartz lamp controlled to provide a thermal load with a differing phase than the mechanical load. Testing cycles can be run for the test object, with impingement cooling permitting the removal of the thermal load between cycles. The test facility emulates operating conditions in a gas turbine engine to impose realistic thermal and mechanical fatigue stress on the test component.

24 Claims, 30 Drawing Sheets

Rim Temp. Reach 950 F, and Bore Temp. Reach 450 F @ 30 Sec

Thermal Buckling Mode I

Buckling Temp. Gradient (ΔT = 155 F)

Buckled Shape

- Waspaloy
- Const. Coef. Of Thermal Expan.
- Axisymmetric Model (7.5 Mil Mesh)
- Fixed Displacement at Bore
- 600 F Bore Temp.

Bore inlet impingement cooling flex lines

Bore Impingement Cooling Piping

SYSTEMS AND METHODS FOR PRODUCING THERMAL MECHANICAL FATIGUE ON GAS TURBINE ROTORS IN A SPIN TEST ENVIRONMENT

CROSS-REFERENCE TO RELATED APPLICATIONS

This application claims the benefit of U.S. Provisional Application No. 61/132,686, filed Jun. 20, 2008, the entire disclosure of which is hereby incorporated herein by reference.

STATEMENT REGARDING FEDERALLY SPONSORED RESEARCH OR DEVELOPMENT

This invention was made with government support under Contact No. FA8650-05-C-2528 awarded by the United States Air Force. The government has certain rights in the invention.

BACKGROUND OF THE INVENTION

The modern gas turbine engine flow path undergoes a dramatic series of axial temperature changes from fan inlet to low turbine discharge. Because the flow path is a near closed system, isolated from the components inboard and outboard, the blades, vanes, and disk rims contained within the system reach operating temperatures up to 2500° F. (surface temp.) in the gas path, and 2500-3200° F. rim temperatures in the high turbine. Conversely, the disk webs and bores which are inboard of the flow path are located in cavities isolated by rotating labyrinth seals and pressure balanced to prevent ingestion of hot gasses into the engine core.

Secondary flow systems, precisely designed, keep disk bores and drive shafts at lower temperatures to limit blade radial growth and maximize material structural properties. Maintaining and controlling thermal gradients between disk rims and bores controls transient disk/blade growth and minimizes tip rubbing and resultant aerodynamic performance loss.

The rim-to-bore thermal gradients represent an additional stress component in conjunction with the rotational stress. In many cases the thermal stress contribution can exceed the mechanical stress. There is also phase lag between mechanical and thermal stresses. The more isolated and massive the disk bore, as in the high turbine, the greater the phase lag becomes. The phase problem is also affected by operability since power manipulation, to a certain extent, determines the severity of the gradient. This creates a situation where different operators may experience inconsistent rotating component life strictly based on how they operate their engines.

Structural integrity personnel have the challenge of trying to establish a life limit for components with simultaneously changing elastic/inelastic strains and material behavior. Data derived from material coupon testing is of limited value because there is no current material testing method (outside of an actual jet engine) that induces a radial thermal gradient in synchronization with realistic in-service rotational speeds. In other words, there is no method that simulates a thermal and mechanical fatigue (TMF) load cycle.

Given the extensive testing used to generate durability and life prediction models, and the cost of full-up engine tests ($6M+each), no cost-effective way to conduct representative TMF testing is presently available. Current component design methods are also very costly, often requiring several iterations to achieve a "best effort" solution, resulting in increases of many millions of dollars and months of schedule to an engine program.

Additionally, TMF related failures in engine hot sections are a critical factor driving class A mishaps, and low Total Accumulated Cycles (TAC) useful life, Mean Time Between Failure (MTBF), and Mean Time Between Maintenance (MTBM). Advances in design that come from better testing have the potential to produce components that are more resistant to the effects of TMF, helping more advanced engines reach 4300 TAC life for the hot section, and help legacy engines extend hot section life to 5000 or perhaps 6000 TACs. Such improvements in component durability could save the USAF hundreds of millions of dollars in future maintenance cost avoidance. Combined DoD and commercial market savings might reach billions of dollars.

Analytical based life prediction systems have fallen short in assessing component life with the result of imposing financial burdens on operators for replacement parts. While analysis tools exist that can model engine components and TMF loading, the results of such model analyses may not adequately predict the response of objects and materials subjected to the environment typically encountered in the gas turbine engine. For example, estimates or assumptions made in constructing such a model may have an exaggerated or underrepresented impact on the test results. Correlation between physical test results and predicted results can sometimes vary widely, often leading designers to specify conservative estimates for predicted lifetimes of engine components.

Commercial and military hot section components are typically retired after a specified number of cycles, or TACs, for which a given hot section component is rated. The particular number of cycles or TACs for which a component is rated is based in part on the particular component. It is commonly believed that there is additional useful life in components retired for reaching the specified number of cycles of TACs. For example, engineering conservatism due to lack of knowledge regarding material behavior under severe TMF conditions typically results in shorter prescribed lives for hot section rotational components. Programs such as ERLE (Engine Rotor Life Extension) seek to validate, through better testing methods, that current component designs do indeed have longer useful lives. It is predicted that significant cost savings per year could be realized by not retiring components too early.

To date, spin pit based TMF testing has been somewhat impractical due to the lack of high heat flux ovens capable of duplicating engine thermal excursions. Prior tests have been conducted with cyclic speeds but constant gradients. The constant gradients typically have been created with induction or resistive element heaters. In the case of turbine hot section components, rim temperatures can reach 2500° F. or higher.

SUMMARY

In accordance with the disclosed systems and methods, a controllable, high-heat flux source provides selective high-heat flux to impose thermal loading on a test object. The test object may be located in a spin test facility and subjected to mechanical loading by high rotational speeds being imposed on the test object. According to an embodiment, thermal and mechanical loading are simultaneously imposed on a test object to effectively reproduce operating conditions in a gas turbine engine environment. The high-heat flux source can be closely coupled to the component under test while the component rotates. The controllable high-heat flux source can be cycled to apply thermal loading on the component in conjunction or in synchronization with rotational or spinning cycles. For example, thermal and mechanical loading can be applied to the component under test by applying the high-heat flux from the high-heat flux source to the component while also spinning the component at high rotational speeds. The thermal and mechanical loading can be applied in different phases and to different extents to reproduce realistic loading conditions on the test component. For example, the realistic loading conditions can emulate those found in a gas turbine engine, where the component under test is a turbine rotor or turbine rotor simulation for such an engine.

According to an exemplary embodiment, the high-heat flux source is a quartz lamp closely coupled to the test component. The quartz lamp can provide localized high-heat flux, such as to a rim area of the test component. The quartz lamp can be controlled to apply a high-heat flux to the rim area of the test component or in relatively tight annuli to produce a thermal gradient in a radial direction of the rotating test component. Power to the quartz lamp can be modulated to produce the desired high heat flux to be applied to the test component. The use of the quartz lamp permits the creation of a controllable gradient on the test component that can be imposed and removed as desired to provide a flexible and simplified test environment for applying arbitrary thermal and mechanical loads to a test component.

According to another exemplary embodiment, a cooling fluid source is provided to a test facility that is used for thermal and mechanical loading of a test component. The cooling fluid source may provide impingement cooling air, for example, to contribute to controlling a temperature or thermal gradient in the test facility or for the test component. The cooling fluid can be provided to various locations within the test facility or onto the test component. For example, in the case of a gas turbine engine rotor, cooling fluid can be directed in accordance with various geometries to a rim, a web, or a bore of the rotor. Impingement cooling air can, for example, contribute to controlling a temperature or thermal gradient imposed on the test component to modulate or otherwise control the temperature or thermal gradient imposed on the component. In addition, impingement cooling air can contribute to cycling thermal loads on the test component.

According to another exemplary embodiment, a control system is provided to permit selected thermal and mechanical loading and cycling on a test component. The control system may include a user interface that permits a user to provide set points or other control input settings for operation of the test facility. The user interface may also permit the user to receive information in the form of outputs to the user interface. For example, the user interface may include audio output devices, such as speakers, horns, bells or other items that produce audible sounds to provide information about a test or the test facility. The user interface may also or alternatively include a visual output device, such as lights, a display or other items that produce visible output to provide information about a test or the test facility.

The control system can be used to set a profile for thermal and mechanical loading on the test component, as well as to control for limits on parameters, for reasons such as safety or component integrity. Controls can be provided to permit set point or other control parameters to be changed or updated during a test to permit real time changes or control, i.e., "on the fly." The control system permits implementation of control strategies, including thermal control strategies, to contribute to minimizing cycle time, including thermal cycle time, to reduce testing duration and cost.

According to an embodiment, spin pit testing i.e., high speed rotational testing, can be used in conjunction with thermal loading for phased thermal mechanical fatigue testing for a variety of differently sized rotating components used, for example, in gas turbine engines. Design and implementation of rotor components, such as, for example, lighter compressor rotors or heavier turbine rotors can benefit from the availability of such testing. In accordance with the disclosed system and method, a high heat flux system is combined with a spin pit test rig, and controlled to be in synchronization with a rotational speed of a test object to permit cycling of both temperature gradient and speed in accordance with desired cycle parameters and values. The combination of the controllable high heat flux system in conjunction with the spin test rig, provides an environment suitable for emulating actual engine operating conditions. Any type of device suitable for acting as a heat source may be used to generate a high heat flux that is controllable to be applied to a test object, such as a rotor.

According to an exemplary embodiment, multiple quartz lamps are used as a heat source to generate the controlled high heat flux. In an exemplary configuration, multiple quartz lamps with reflector configurations that focus the heat flux may be used. The reflector configurations may be cooled with a cooling source that can be arranged as a cooling enclosure supplied with a cooling liquid, such as water, for example. Temperature feedback sensors can be provided to the quartz lamps and/or reflector configurations to obtain a control parameter for applied thermal loading.

In an exemplary embodiment, the test facility may provide rotational spin testing to impose mechanical loading, such as with speeds of 40,000 RPM for example. The mechanical loading can be applied in conjunction with thermal loading, variable thermal loading, thermal gradients and/or variable thermal gradients. For example, thermal gradients in the range of temperatures discussed above can be applied in synchronization with mechanical loading.

The mechanical loading imparted by the spin testing and the thermal loading can be determined by measuring strains at given speeds and temperatures. For example, measurement or sensing devices are employed in the test facility to permit measurement of strains at speeds of 40,000 RPM with and without thermal gradients.

According to an embodiment, a desired radial thermal gradient is achieved by focusing thermal energy to limit stray thermal radiation. The thermal gradient may be generated by directing a high heat flux source to specific locations on the object under test. The high heat flux source may produce high heat through induction, laser, quartz lamps, focused quartz lamps, impingement, resistive or other sources capable of generating high heat flux. Advantageously, the test facility may include heat rejection devices or employ heat rejection methods to improve heating efficiency.

According to an embodiment, significant representative thermal gradients are imposed on full scale rotating turbine engine components in a Low Cycle Fatigue (LCF) spin test facility environment. The spin test environment may include a soft vacuum, and may be operated, for example, at 1 atm. The test facility may include heating and cooling equipment and associated instrumentation and control systems. The instrumentation and control systems can be used to develop thermal control strategies capable of inducing realistic thermal gradients into rotating objects, such as of typical size, mass, and materials in relation to gas turbine engine components, for example. An example of a representative component upon which realistic testing conditions are desired to be imposed is a bladed High Pressure Compressor (HPC) rotor.

Typical thermal gradients imposed on a high compressor rotor sample in the test facility are established with temperatures in the range of from about 1000° F. to about 1400° F. at the rim and in the range of from about 300° F. to about 600° F. at the bore, with a linear or nonlinear distribution or combinations of linear and nonlinear distributions.

BRIEF DESCRIPTION OF THE SEVERAL VIEWS OF THE DRAWINGS

The disclosed system and method are described in greater detail below, with reference to the accompanying drawings, in which.

DETAILED DESCRIPTION OF THE INVENTION

Figure 1:
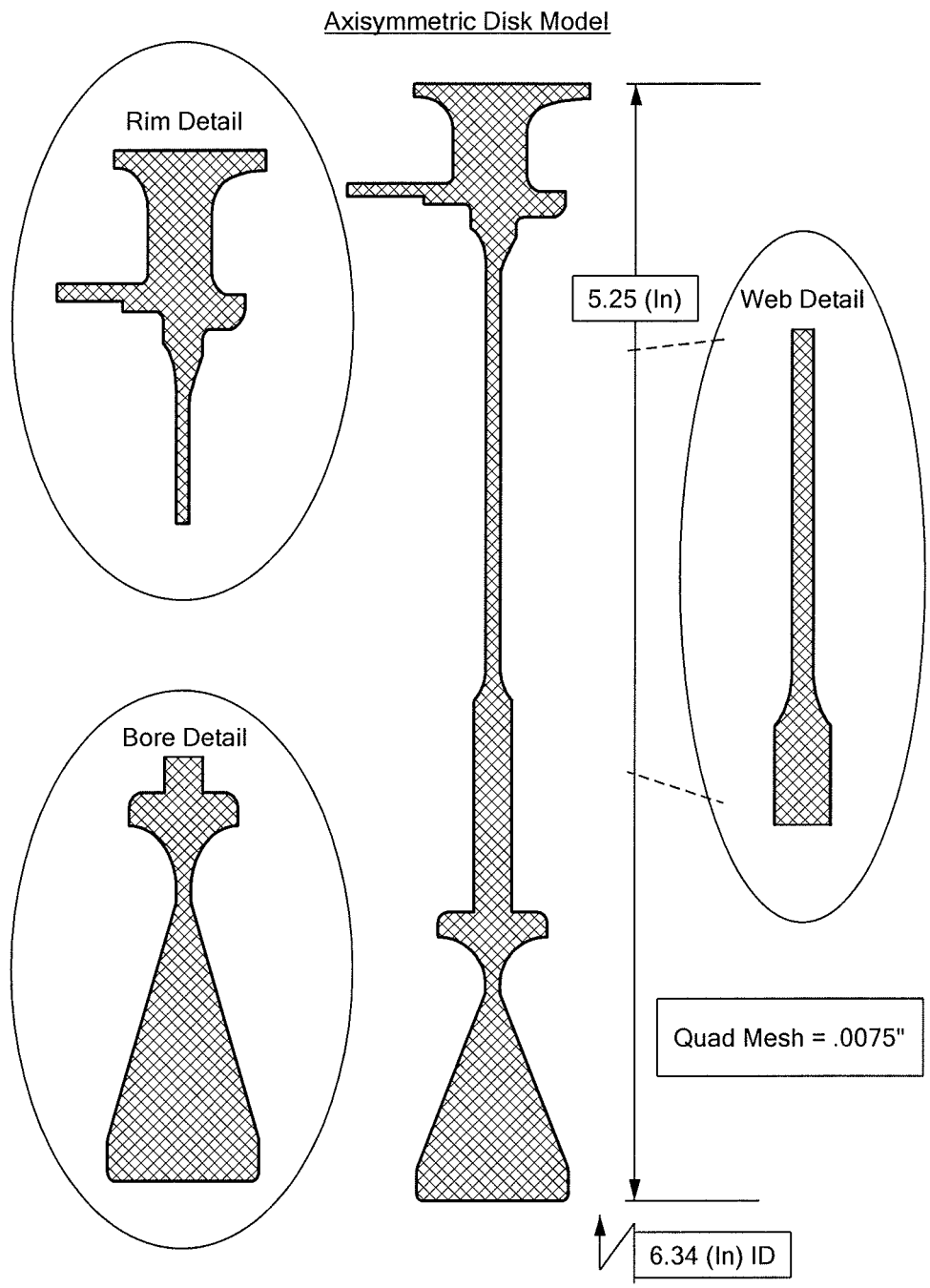
FIG. 1 is an illustration of an axisymmetric disk model.

The entire disclosure of U.S. Provisional Application No. 61/132,686, filed Jun. 20, 2008 is hereby incorporated herein by reference.

It is generally accepted that there is the potential for determining significant additional safe operating life in gas turbine engine components. Extending the useful service life for such engine components represents a considerable savings to the Department of Defense (DoD) and commercial aero turbine and industrial gas turbine operators. Correlation of FEA models with empirical thermal gradient testing can help reduce the risk of deviating from current conservative life estimates and potentially lead to certification of engine components at a greater number of cycles or Total Accumulated Cycles (TAC's) before they are retired. Such certification may save commercial and institutional operators, including military or other governmental operators, significant costs by increasing the time between inspections and reducing the amount of spare parts in inventory used to meet readiness specifications for fleet aircraft.

Testing gas turbine engine components can be challenging, especially if the components are to be tested in environments that emulate realistic gas turbine engine conditions. In part, because of the challenges of testing gas turbine engine components, it is difficult to determine an operational life for engine components. There is a general tendency to provide conservative estimates for engine component lifetimes, in view of the limited available data due to the difficulties of conducting realistic testing on components. Due at least in part to such conservative estimations, it is generally accepted that there is the potential for significant additional safe operating life times for gas turbine engine components. Additional safe operating lifetime knowledge concerning gas turbine engine components can help extend the useful service life for components, which represents considerable savings to military and commercial users of gas turbine engines.

During the operation of a modern gas turbine engine in aero applications, for example, the turbine and compressor rotors undergo simultaneous rapid changes in rotational speed and temperature, i.e. throttle advance for ground idle to takeoff, maintain high speed and temperature for a certain dwell time and return to ground idle and shut down.

During these transient and steady state operating points the rotating hardware, in particular the turbine and compressor disk(s), sustain large temperature gradients between the inner diameter (bore) and the outer diameter (rim). These temperature gradients are desired, and are designed, to maintain cooler interior engine temperature, i.e., to protect oil sumps and bearings from excessive temperatures. However, in establishing these gradients, and maintaining the operating temperature, large thermal stresses are induced in the disk, that are in addition to the mechanical stresses, such as centrifugal stresses, for example, caused by high rotational speeds. Also, during transient engine operation, or acceleration/deceleration of the engine/disk, there is a phase difference, or lag, between mechanical and thermal stress. Mechanical and centrifugal loads are applied or removed more rapidly than the thermal loads.

By thermal and centrifugal cycling of a disk, such as a rotor, in a controlled environment, a better understanding of centrifugal/thermal interaction can be gained, and can be used to obtain a clearer understanding of residual disk life. Such an understanding can provide opportunities to design longer life disks, and reduce the risks of extending the disk service life.

In accordance with the presently disclosed systems and methods, thermal and mechanical loading are applied to a test object in accordance with the present disclosure, to emulate operating conditions in a gas turbine engine, for example. The parameter values for the loading to be applied to the test object, which can be a high compressor rotor from a gas turbine engine, are accordingly selected based on conditions observed in such an engine. For example, a typical thermal gradient applied to the rotor results from temperatures in the range of from about 450° F. to about 1400° F. at the rim and in the range of from about 300° F. to about 600° F. at the bore, with a linear or non-linear distribution or combinations of linear and non-linear distributions. The above gradients may be applied to a rotating rotor that may have a rotational speed in the range of from about 1200 RPM to about 40,000 RPM.

In accordance with the present disclosure, the test facility provides the thermal gradient and rotational loading provided in the test facility can be controllable to produce desired test profiles and cycles. A desirable test cycle interval may be in the range of from about 30 seconds to about 300 seconds. As part of the cycle time, the rim of the rotor may be heated from ambient to a desired thermal peak (such as indicated above) to establish a desired gradient in approximately 30 seconds or less. For example, the disk rim may be heated from ambient (300° F.) to a peak temperature of 950° F., for example, in 30 sec.

Similarly, a cool down time to reduce or remove the thermal gradient established on the rotor is desired to be in the range of from about 30 seconds to about 120 seconds. These types of temperature, thermal gradients, speeds and cycle times are typical of desired TMF loading. However, the test facility according to the present disclosure can provide a wide variety of thermal and mechanical loading values, including those mentioned above, as well as other ranges available within the disclosed control system.

Because of the limitations on the available data due to the difficulties of testing gas turbine engine components, designers often employ modeling analysis using simulations, including finite element analysis (FEA) models, with thermal and mechanical loading simulations to help validate or understand operational lifetime estimates. For example, thermal analysis of gas turbine engine components can be conducted with software analysis tools such as ANSYS®. Analysis tools such as ANSYS can be used to provide predictions for responses to thermal and mechanical loading on the test objects in the test facility. For example, an analysis tool can be used to predict biaxial stresses on a rotor that can be compared against actual measurements to determine the validity of the modeling predictions derived from the analysis software.

Modeling and analytical tools for analysis of test objects to confirm or predict responses to thermal or mechanical loading can be used in accordance with the present disclosure. For example, FEA models have been used to predict life estimates for gas turbine engine components. By correlating FEA models with empirical results of thermal and mechanical loading in accordance with the present disclosure, a risk of deviation from current conservative life estimates can be reduced, and permits the possibility of identifying design factors for contributing to increasing life estimates, or may potentially lead to certification of components at a greater number of TACs prior to retirement of a given component.

An exemplary gas turbine engine component, which may be a tenth stage compressor rotor for a gas turbine engine, can be used as a test object in the TMF test facility. The tenth stage compressor rotor is also referred to herein interchangeably as a disk or rotor, and is meant to be inclusive of the usage of the terms test object or test component. Prior to conducting actual testing, a model of the component can be developed using analytical tools, such as software analysis tools discussed above, to determine or predict responses of the component to applied TMF loading. The test component may be an actual gas turbine engine component, a simulation of a component, a portion of a component or any other type of desired test object for which TMF loading is desired. A test component geometry can be developed and input into a model based on component drawings or other representations, such as computer generated representations. For example, a Unigraphics (UG) model can be generated and an ANSYS mesh can be made. Such a model can be used for preliminary/final analysis including, but not necessarily limited to, the following:

Thermal radiant heating predictions
Impingement cooling predictions
Disk buckling analysis
Thermal stress analysis
Centrifugal analysis
Deflection analysis In addition to disk geometry in this example, the effects of the blade masses are included. The term "blade" includes a dovetail portion used for connection with the rotor component. In the present example of a tenth stage compressor rotor, six (6) representative blades were weighed, the center of gravity was estimated for each, and a +3σ weight statistical distribution was calculated. The +3σ blade weight times the number of blades (92) are modeled as a point mass at the blade center of gravity (CG). This blade model introduces blade loading into the disk rim. Table 1 shows the blade weight calculation.

TABLE 1

| Blade | Wt1 (gm) | Wt2 (gm) |
|---|---|---|
| 1 | 12.400 | 12.400 |
| 2 | 13.300 | 12.300 |
| 3 | 12.100 | 12.100 |
| 4 | 12.500 | 12.600 |
| 5 | 12.700 | 12.800 |
| 6 | 12.500 | 12.800 |
| Avg | 12.583 | 12.500 |
| Dev | 0.367 | 0.258 |
| Total Wt | 75.500 | 75.000 |
| Total set wt | 1157.667 | gm |
| Total set wt | 2.549927 | Lb |
| +3sig wt | 3.651062 | Lb |

FIG. 1 shows the final ANSYS disk model.

Figure 2:
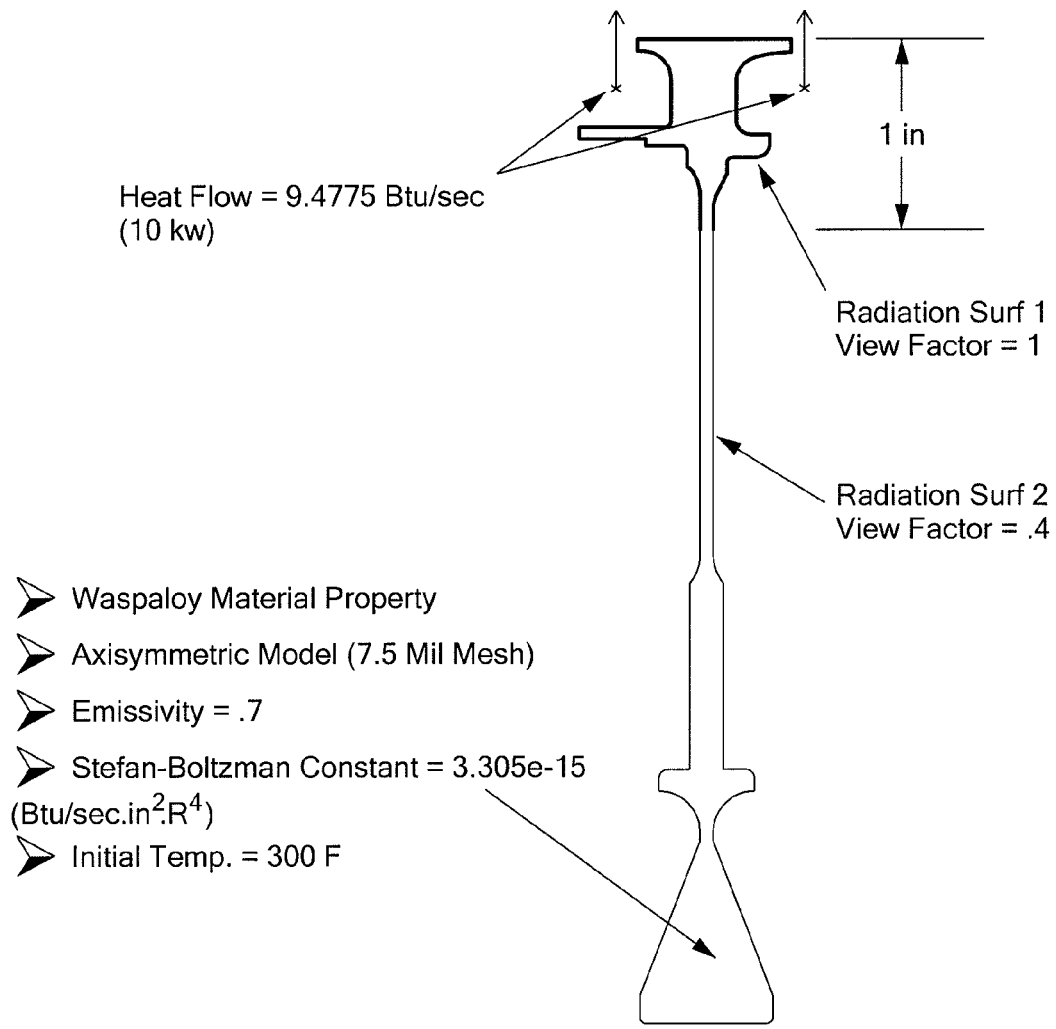
FIG. 2 is an illustration representing an axisymmetric radiation thermal model.

A radiant heat transfer analysis is used to quantify and predict a thermal response of the disk to radiant and conductive heating, and to establish a resulting disk temperature profile. The temperature response of the disk is analyzed using quartz lamps as a heat flux source, each lamp being operated at 10, 20 and 32 kW. Any available power lamps may be used that can achieve a desired thermal profile. In addition, any suitable heat source may be used to conduct the analysis, with potentially different characteristics of the sources being modeled in the analysis. The results of the exemplary analysis are cross plotted to determine a time to temperature versus power and a rim to bore temperature profile. FIG. 2 shows the typical model boundary conditions. The quartz heater input is considered constant, and a parabolic reflector geometry is modeled to produce a radiant energy input that is normal to the disk surface.

Figure 3:
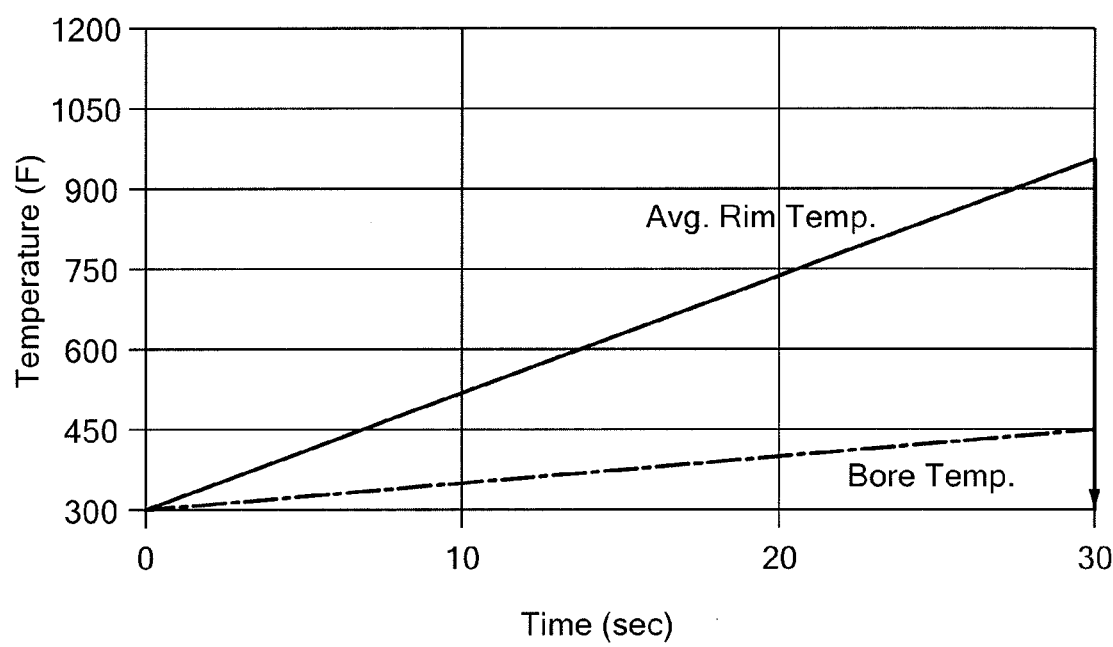
FIG. 3 is a graph illustrating rim temperature and bore temperature vs. time.
Figure 4:
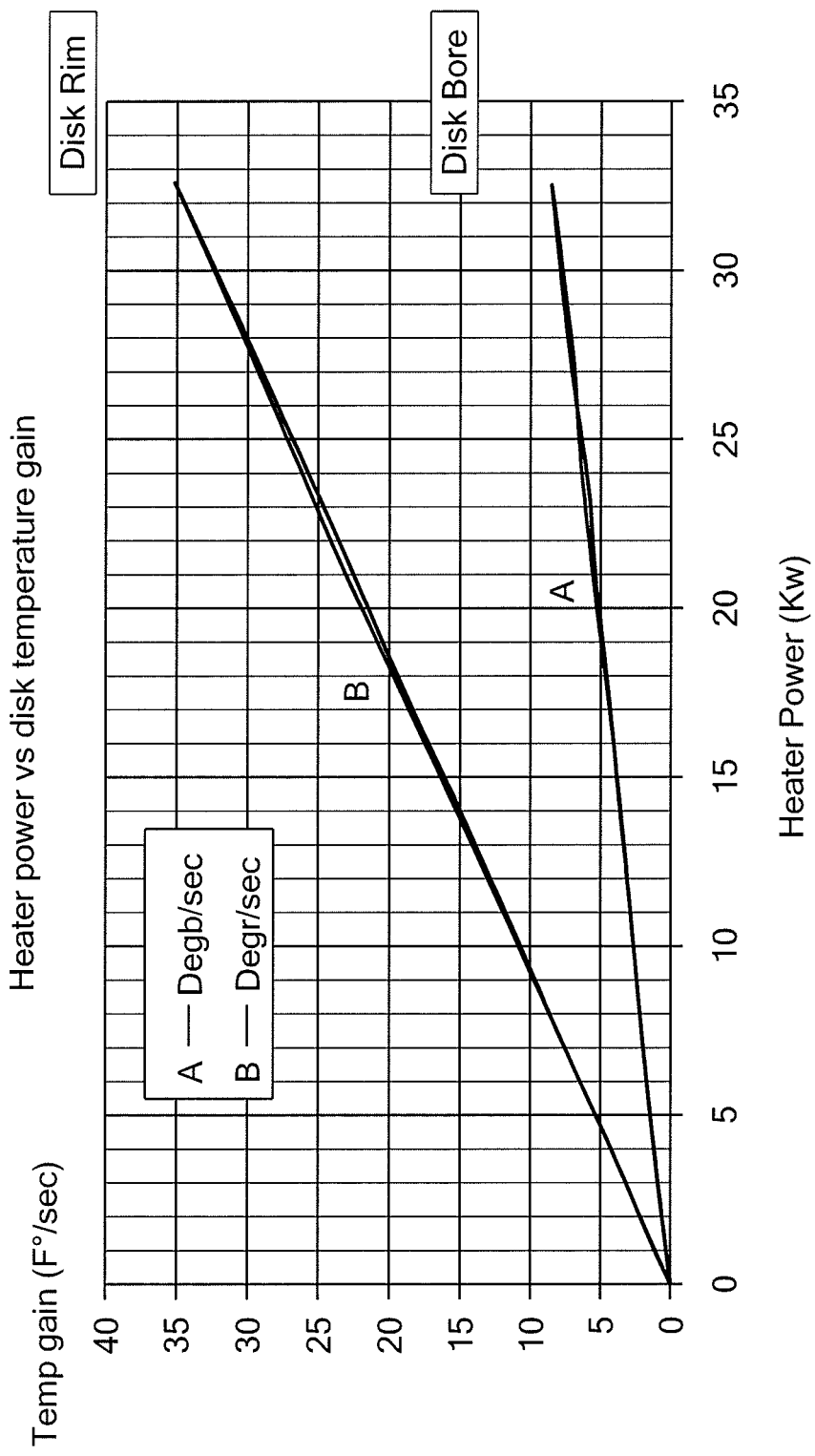
FIG. 4 is a graph illustrating heat power vs. temperature gain for a disk rim and bore.
Figure 5:
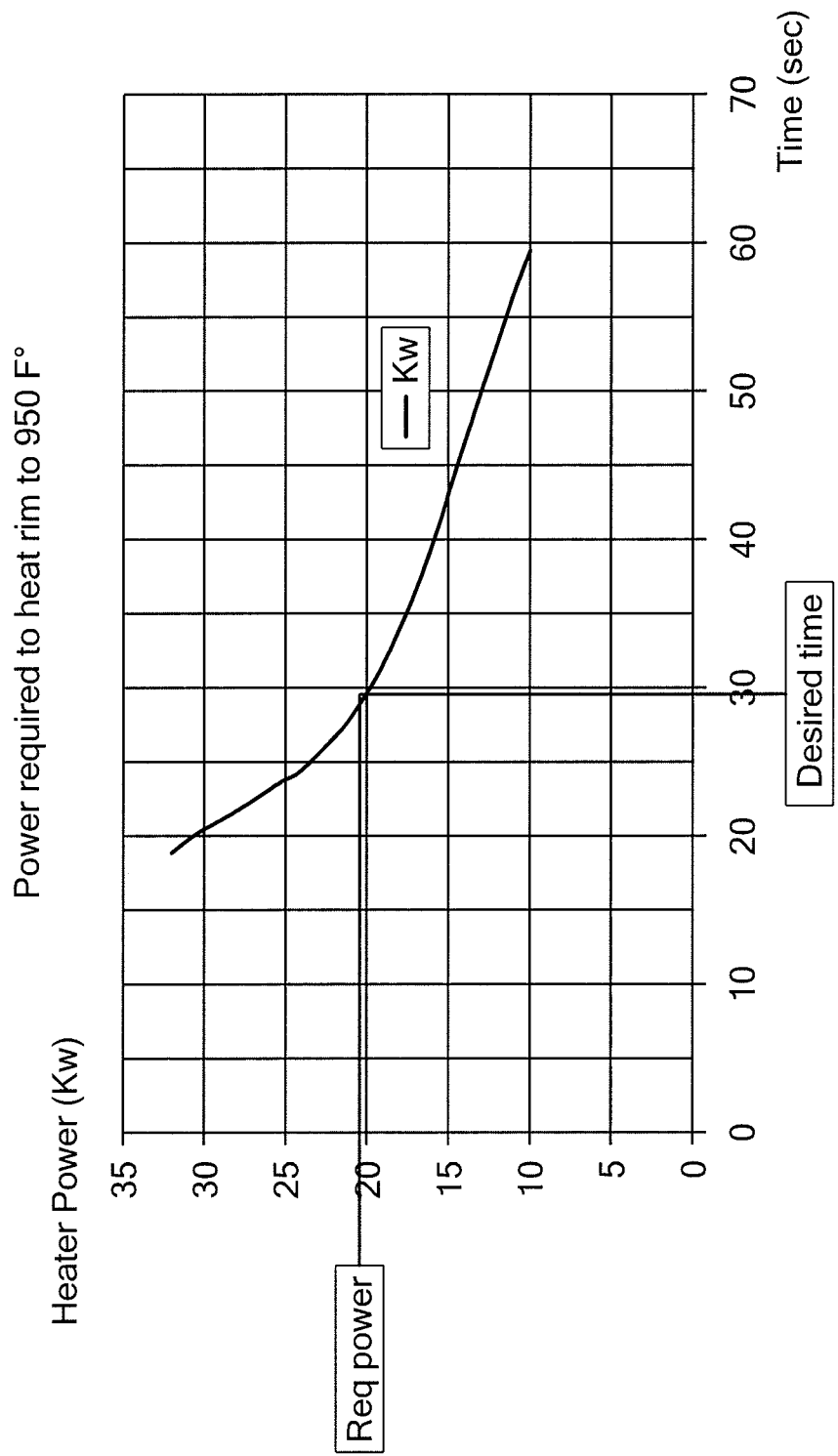
FIG. 5 is a graph illustrating a characteristic curve of power vs. time for heating a rotor rim.

Transient analysis for a 10 kW input is shown in FIG. 3, which illustrates transient temperature response, in which the bore and rim temperature versus time can be predicted. By completing the same analysis at various power levels, such as 20 and 32 kW, an estimate of the power, time and disk temperature profile can be made. The results of these analyses are shown in FIG. 4 and FIG. 5, illustrating heater power and time to temperature, respectively.

The ANSYS model previously developed is used to perform a convective heat transfer analysis. The system response is assessed at various convective heat transfer coefficients, and parameter values are determined for use in setting up the disclosed test facility. Also, separate rim and bore impingement cooling effects are analyzed and the effects are quantified.

Figure 6:
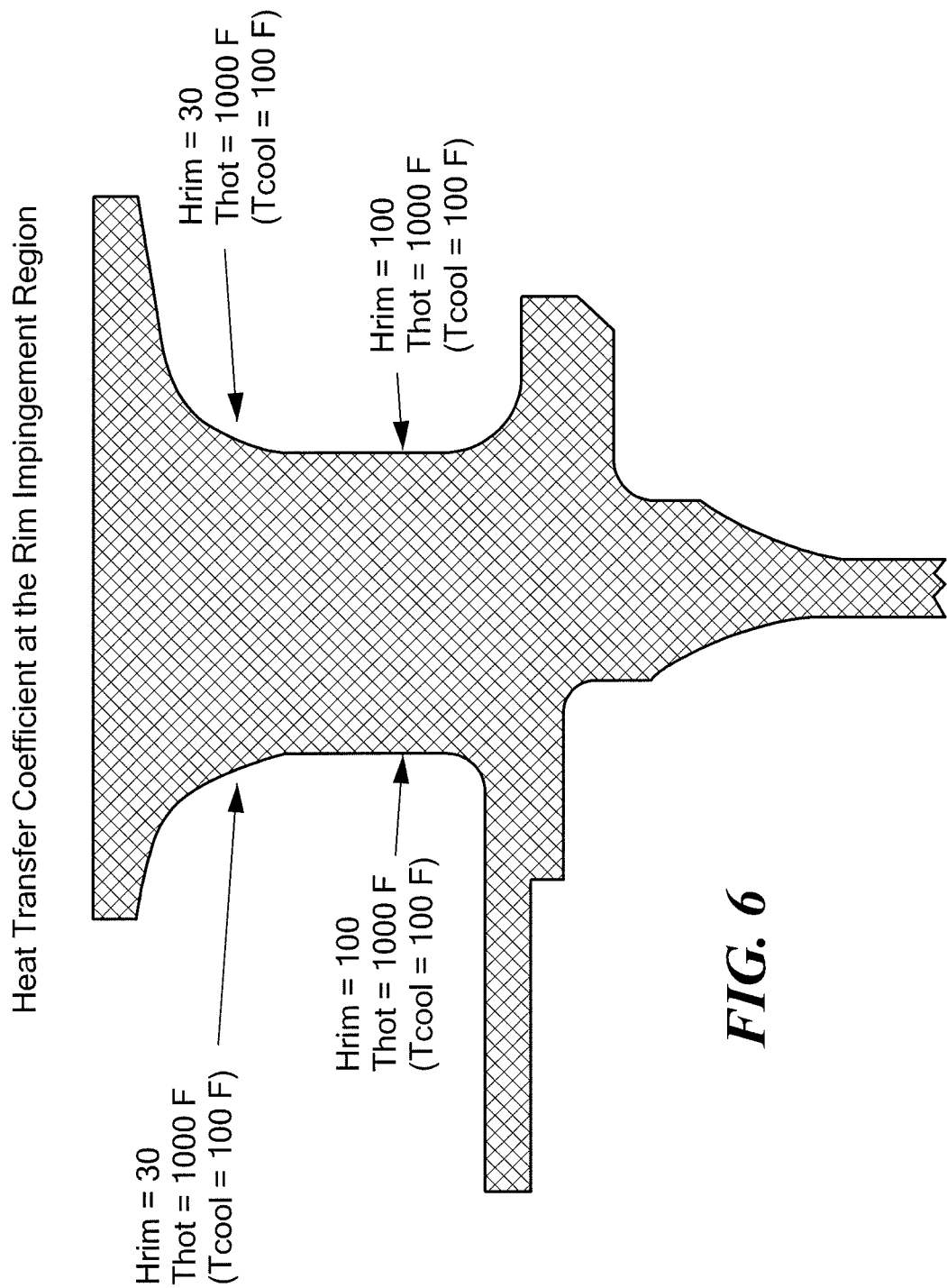
FIG. 6 is an illustration of a representation of heat transfer coefficient at a rotor rim.

The heat transfer coefficients (h) in various areas of the modeled rotor are estimated, using known analytical methods. FIG. 6 illustrates disk boundary conditions and results of the convective heat transfer analysis.

Figure 7:
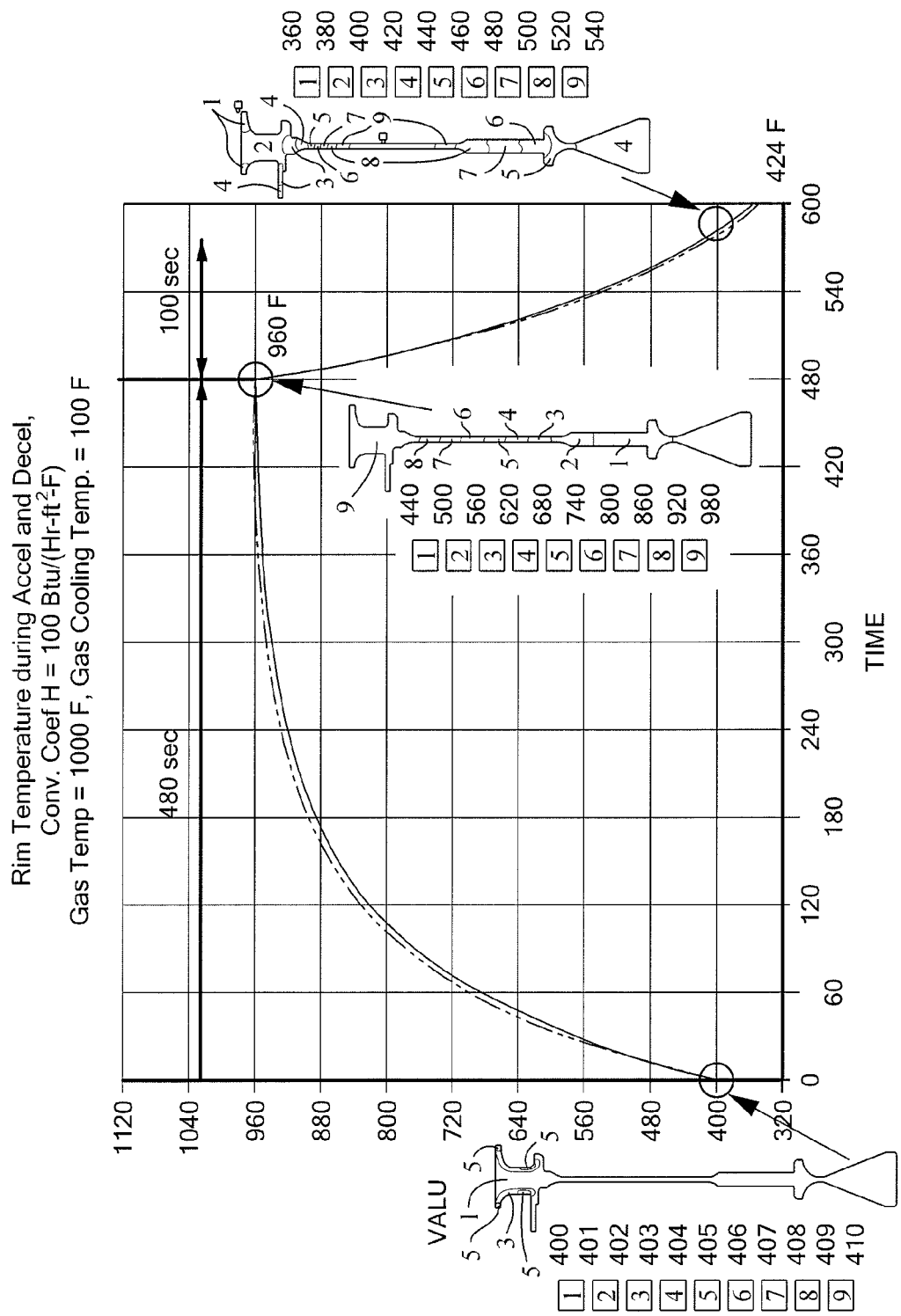
FIGS. 7-9 are graphs illustrating predicted rim temperature characteristics for different heat transfer coefficient values associated with a heating method according to an exemplary embodiment.
Figure 8:
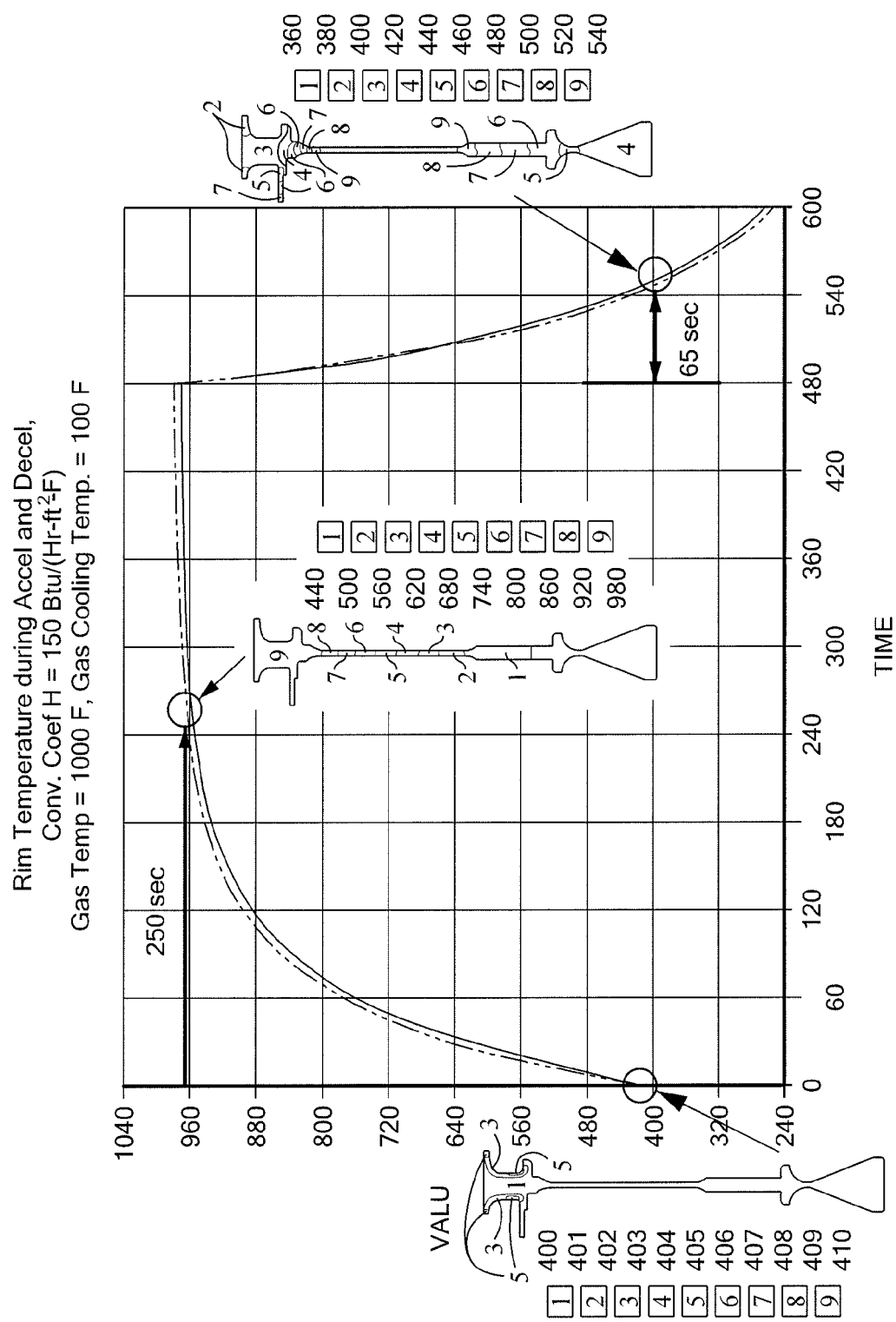
Figure 9:
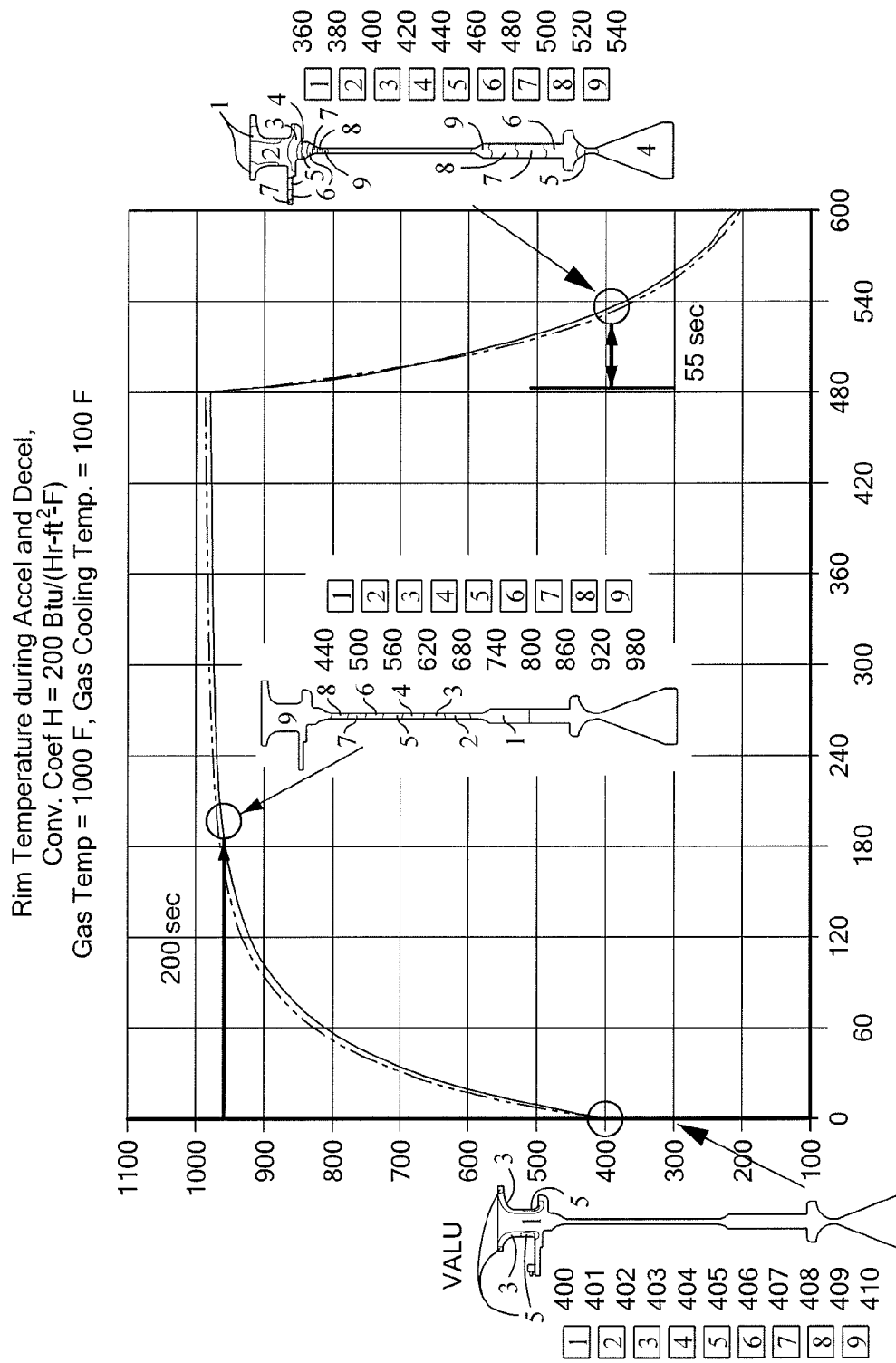

To determine a disk temperature profile versus time, a transient heat transfer analysis is completed. A typical transient response is shown in FIG. 7. It should be noted that FIG. 7 shows the disk response to both convective and impingement heating and cooling. The results are used to analytically predict the effectiveness of the test facility, in particular for the heating and cooling systems. The analysis is performed for various h values: 100, 150 and 200 (BTU/hr-ft$^{2\circ}$ F.). The results of the analysis for the above h values are respectively shown in FIGS. 7-9.

The analysis with respect to an impingement cooling system that can be employed in the test facility produces several useful predictions. For example, the analysis predicts that adequate disk cooling time for the example rotor is achievable. The analysis further indicates that a temperature inversion from the rim to the bore of the example rotor can occur, which may lead to critical buckling modes. In addition, the analysis indicates that the system is sensitive to the h value. This analysis information, along with the radiant heating analysis, is used to determine a test facility configuration and a TMF testing cycle for the example rotor.

Based on an adequate flow rate, such as, for example, 1 lbm/sec, 70° F. shop air, and set up choices made for the example rotor, e.g., impingement cooling air nozzle placement, a value of h of 100 (BTU/hr-ft$^{2\circ}$ F.) is estimated and used in all further calculations. The h value is a measure of test object thermal response, and is estimated based on the above analysis. The actual disk response may be faster, indicating a higher h value being achieved, or slower, indicating a lower h value. In practice, test facility parameters can be adjusted to compensate for variations in the estimated h value based on empirical results.

The above analysis indicates that a reverse temperature gradient on the disk is possible, i.e., the rim temperature is less than the bore temperature. This situation may occur during testing, for example, if the bore cooling is not as effective as the rim cooling and/or the bore ambient temperature slowly "creeps" higher over time causing an inverted temperature profile. As a consequence of this temperature inversion, the disk web may buckle causing a mechanical failure. A disk mechanical analysis is performed to calculate a critical temperature that may cause this phenomenon. The previously discussed ANSYS model is used to calculate the buckling load. It is desirable to obtain a conservative prediction of the lowest temperature difference that causes the fundamental buckling mode to help ensure that critical buckling modes are avoided. Accordingly, zero (0) rotational speed is assumed for the calculations involved in the above analysis.

Figure 10:
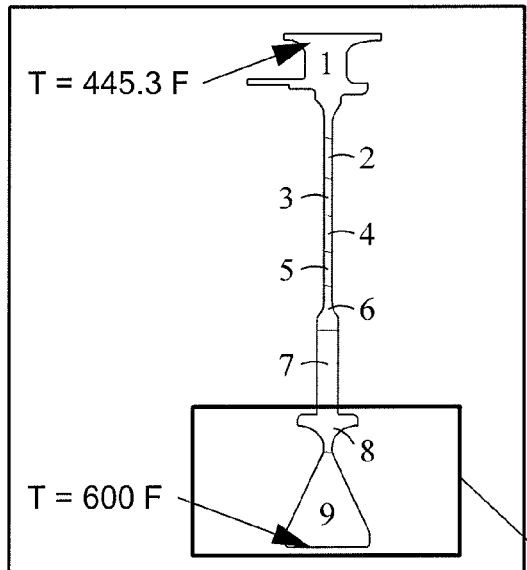
FIGS. 10-11 are illustrations showing mechanical modeling of a rotor for thermal buckling analysis.
Figure 10:
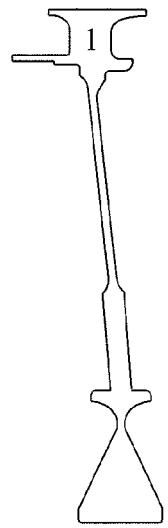
Figure 10:
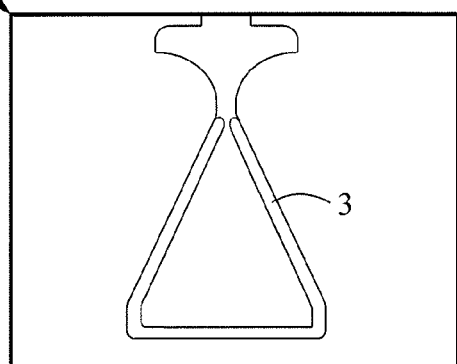
Figure 11:
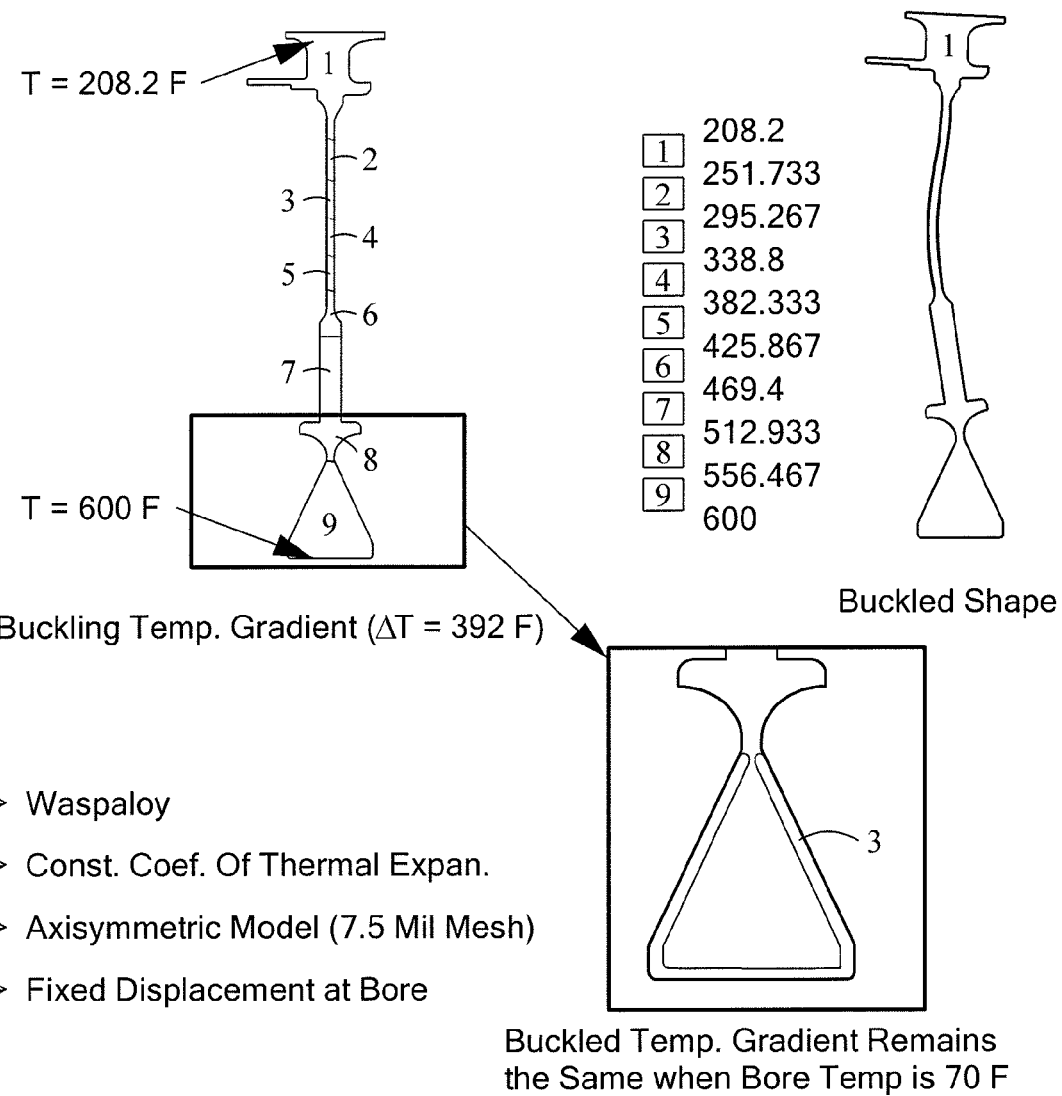
Figure 12:
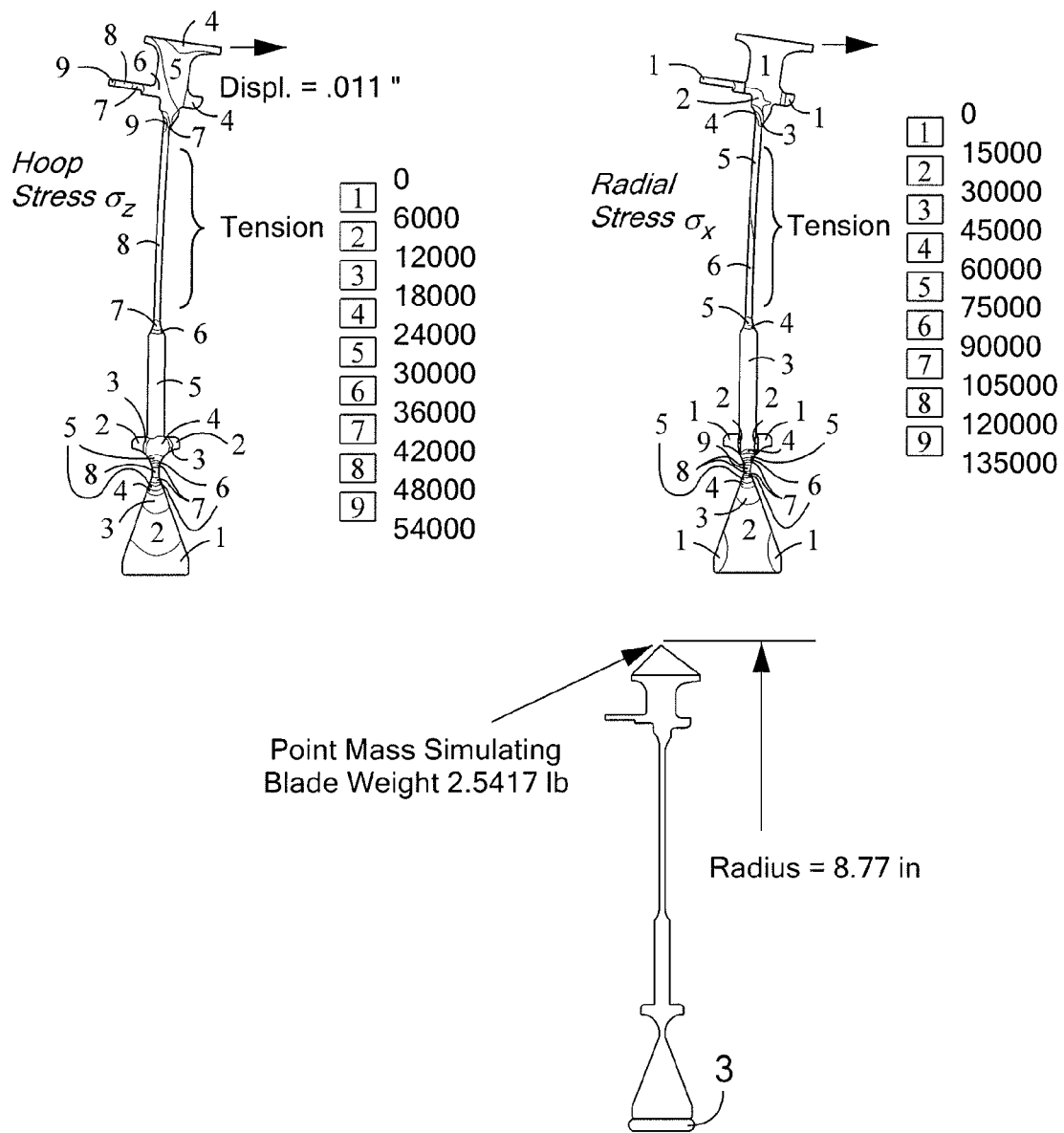
FIGS. 12-13 are illustrations showing modeling of rim deflection for a typical rotor under rotational stress.
Figure 13:
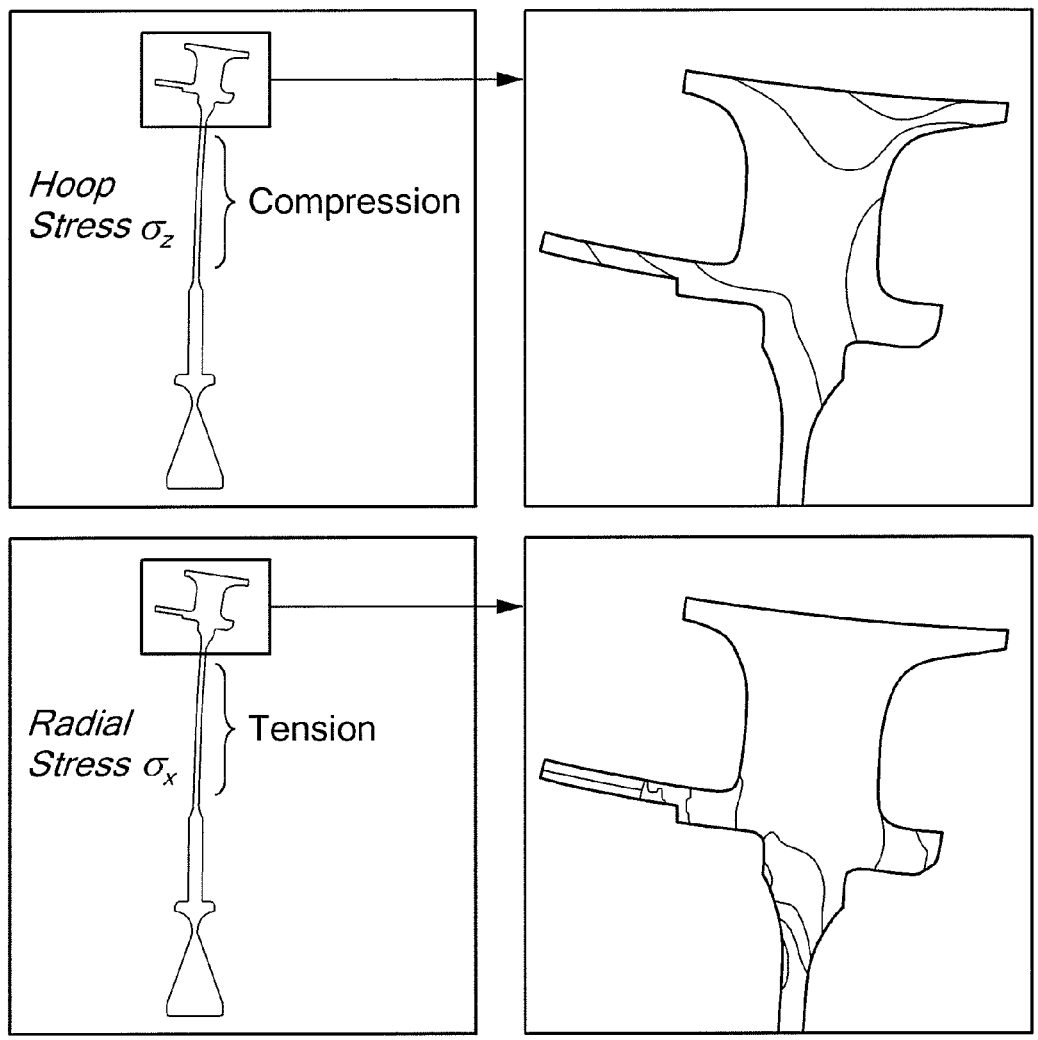
Figure 14:
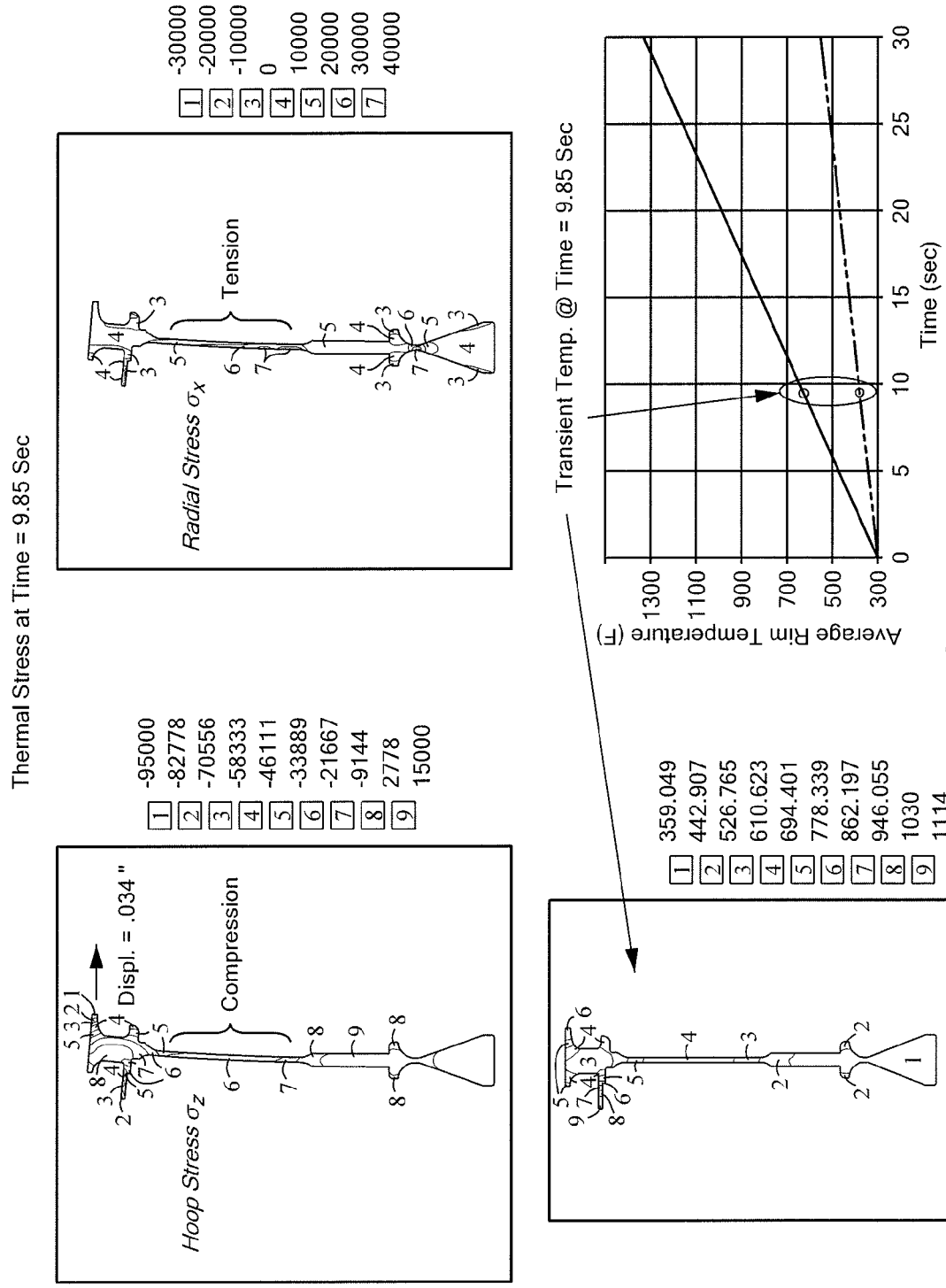
FIGS. 14-15 are illustrations showing modeling of a rotor subjected to thermal and mechanical stress.
Figure 15:
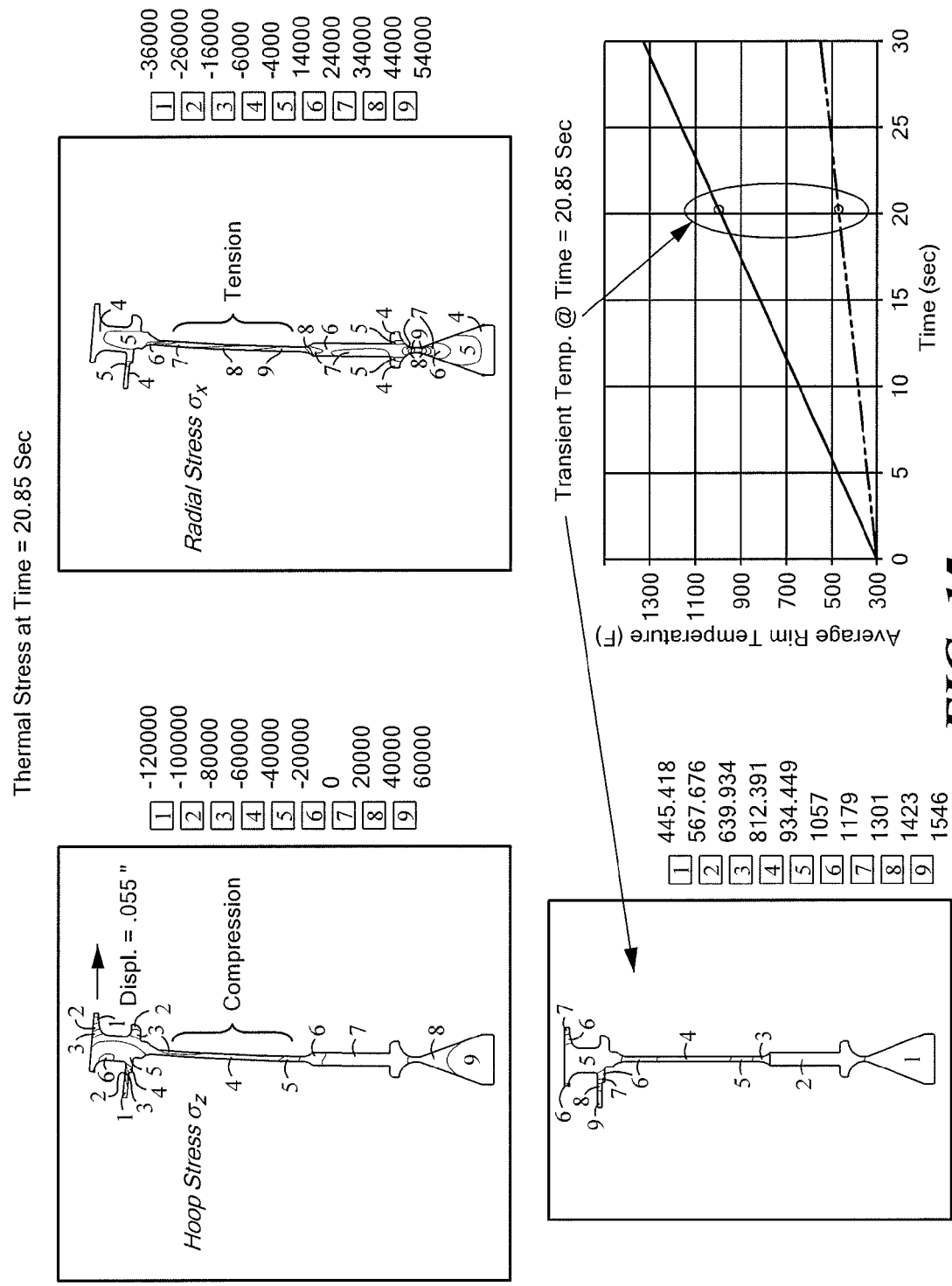

An iterative solution is used to determine a critical temperature profile ΔTrim/bore that may cause the disk to buckle. In the analysis model for the example rotor, the bore temperature is iteratively increased in steps relative to the rim temperature. Using this approach two (2) eigenvalues and eigenvectors are found. Because the analysis is performed with the assumption of no rotational speed, and thus no centrifugal stiffening, a conservative ΔTrim/bore can be determined for critical temperatures or thermal gradients that may cause disk buckling. FIGS. 10-11 show examples of predicted critical buckling modes that may occur at associated critical temperatures.

FIG. 10 shows a fundamental disk buckling mode that is predicted to occur if ΔTrim/bore is about 155° F. or greater at zero rotation speed. FIG. 11 shows another disk buckling mode predicted to occur with ΔTrim/bore being about 392° F. these values can be used to estimate a safe operating range for the example test component during testing. For example, unintended test component critical failure during testing can be prevented by employing a safety alarm, shutdown or other safety response when a given thermal gradient value is exceeded to avoid a critical buckling mode occurrence. In the test facility, two thermocouples can be monitored to calculate the rim to bore temperature difference. An alarm or other safety response is triggered if the ΔTrim/bore becomes greater than, for example, about 140° F., based on the above analysis for the example rotor. An exemplary safety response is to permit the heaters to engage to supply heat to reduce the gradient if the disk is rotating.

Several additional analyses for the example test component are undertaken including thermal and centrifugal deflection analysis to insure adequate stator/rotor (wheel space) clearance during operation, as well as thermal and centrifugal stress analysis to verify that disk stresses, and stress range, are acceptable for the disk material to help prevent or reduce the risk of disk failure during testing. These analyses include the effect, where applicable, of blade weight on the rotor structure. FIGS. 12-15 show centrifugal deflection/stress analysis and thermal deflection/stress analysis results.

The results of the analyses of the example test component are used to define a preliminary test facility configuration and TMF testing cycle for the example test component. For example, the analyses results may be used to determine static and rotating instrumentation usage, to set or control safety parameters, instrumentation limits and/or design parameters for the heating and cooling systems.

It should be understood that while undertaking an analysis of an example test component prior to actual testing can be helpful, it may not be required in every circumstance. For example, known data or established estimates for operational parameters of a given component may be used to define a configuration and cycling for the test facility to test the given component. Prior analysis for a test component may also be used to predict a response to TMF imposed on a different test component where the response to the differences is known or can be estimated with sufficient accuracy.

According to an exemplary embodiment of the disclosed systems and methods, a test facility is provided that can attain a coordinated variable temperature gradient and a mechanical strain gradient on a test object being rotated. The test facility can emulate some of the conditions in a gas turbine engine to impose TMF loading on the test object. With respect to the example rotor as the test object, a rim-to-bore temperature gradient may be implemented with a peak rim temperature of 1000° F. A high density heat flux is applied to the test object rim to establish a peak temperature and a desired temperature gradient across the test object. The temperature gradient may be in the range of about 500° F., which may be achieved, for example, when the peak rim temperature reaches approximately 1000° F.

The test facility may be used for compressor and turbine components for gas turbine engines, for both aero and land based applications, including industrial gas turbines. Pertinent parameter values can be set in the test facility based on the analysis discussed above, or prior actual rotor testing, for example. Quartz lamp power profiles, cycle times, rotational speed profiles and safety set points can all be established for the test facility set up for TMF testing on the rotor.

The rotor disk may be mounted horizontally or vertically, depending upon the test facility configuration. With the example rotor, the disk is bladed, and the blades are loaded against a disk blade retainer. Optional separate blade retainers, such as Ni-chrome strips, may be used, although separate blade retainers are typically not part of the assembly. All blades are retained to the rotor during testing.

The test facility includes a chamber for housing a test component that is to be subjected to TMF loading. A drive motor that has a drive shaft is mounted to permit the drive shaft to extend into the chamber. The drive shaft may be a hollow drive spindle. An arbor may be mounted on the drive shaft that serves as a mounting structure for a test component, such as a rotor. The drive motor can be a turbine drive that operates with a compressed air supply. The compressed air can be modulated to control motor speed, such as with pneumatic control. The chamber can be selectively or partially sealed to permit a variable pressure to be applied in the chamber. For example, pressurized fluid, such as nitrogen gas or air can be introduced into the chamber. In addition, a vacuum can be drawn in the chamber to permit TMF loading to be applied with less interference. In the case of a chamber vacuum, radiant heat sources may be used to impart a thermal load and thermal gradient on the test component. Any type of motor drive may be used to implement the mechanical loading through centrifugal stress, including electrical and magnetic base drives.

Since real time monitoring of the TMF rotor temperatures is desired, sensors can be provided at specific locations in the test facility or on the rotor to track the radial temperature profile. IR sensors can be used for temperature sensing, but may experience interference from the high stray radiation created by a quartz lamp system, which may introduce the possibility of errors in measurement. Surface mounted Type K thermocouples can also be used for temperature measurement.

Figure 17:
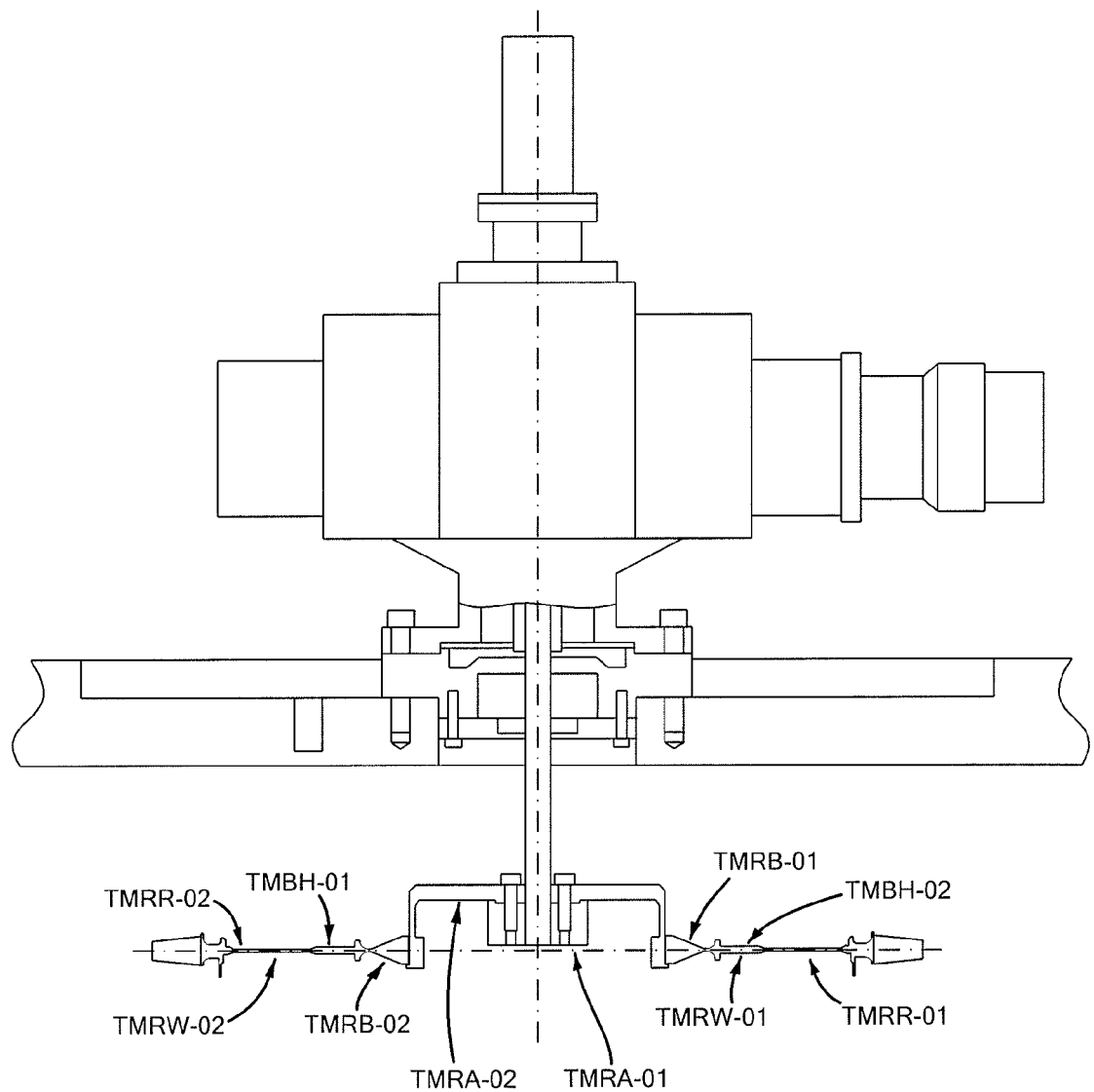
FIG. 17 is a side elevation sectional view of a test facility in accordance with an exemplary embodiment of the disclosed system and method, showing instrumentation applied to a rotor under test.

In the present test example, sets of thermocouples are employed to track a temperature gradient across a disk radius from rim to bore. For example, two sets of four (4) thermocouples may be used and strategically located for temperature measurement and thermal gradient determination. Exemplary locations for the thermocouples are the live rim, web, bolt circle and bore of the example rotor. Optional sensors may be used to monitor blade temperatures. Additional thermocouples are installed within the arbor to monitor thermocouple wire transition points. The Type K wire for the thermocouples is changed to allow a sheathed diameter that would fit into a hollow drive spindle that ultimately terminates at, for example, a 28 contact slip ring. FIG. 17 illustrates thermocouple location for an exemplary configuration of a rotor in the test facility.

High temperature adhesives are used to secure miniature bare TC wires to the disk with appropriate strain loops. At the entrance to the hollow drive spindle the wires are changed to sheathed types to prevent shorting and chafing. The locations of the thermocouples may be selected to produce a balanced weight profile across the disk. For example, desired thermocouple locations may be selected for temperature measurement, and a thermocouple location, or balancing mass location, may be selected to obtain an even weight distribution across the disk. With such a balanced distribution, the disk properties under TMF loading should not be significantly impacted by the instrumentation.

The thermocouples can provide real-time temperature data, and can be used for comparison with a predicted profile. Optionally, static strain gages can be used to measure mechanical stress or loading. Some precautions may be taken to shield the strain gages from excessive temperatures at the rim and web areas. In addition, or alternately, measurement devices such as thermocouples may be located and used to monitor conditions in the test facility itself. For example, additional instrumentation may be used to monitor electrical connections for the quartz lamp and lamp retaining clips. The test facility has a data acquisition system (DAQ) to record and measure disk and wheel space temperature. A controller, such as may be provided in a programmable logic controller (PLC), implements data acquisition by sampling sensors and other device parameters. The acquired data may be used to provide closed loop control for the test facility, and may also be recorded to provide a record of test conditions. The sample rate of the controller is adjustable, so that a variable amount of data can be collected for a given set of TMF loading cycles.

Once the example rotor and/or test facility is instrumented as desired, test cycling may commence to impose TMF loading on the rotor. It should be understood that a variety of instrumentation may be used or omitted in the test facility, depending upon the desired testing and/or test component. In addition, the instrumentation may be used to help control the test facility.

The instrument and control systems provided in the test facility according to the present disclosure permit TMF loading to be applied to a test component in accordance with various profiles or control strategies. For example, a control implementation may use instrumentation feedback to induce a realistic thermal gradient in a rotating disk that emulates a gas turbine engine operational condition. An example of a realistic thermal gradient may have temperatures in a range of from about 450° F. to about 1400° F. at a rim of the rotating disk, and in a range of from about 300° F. to about 600° F. at a bore of the rotating disk. The control strategies may include set points or cycling profiles to achieve desired testing goals, such as to minimize cycle heating and cooling time. In addition, the control strategies can impose coordinated thermal and mechanical loading according to a given profile, such as by setting a particular phasing between application of thermal, and then mechanical loading. The mechanical loading or stress may be in the form of centrifugal stress, for example.

The control system can provide controls to produce a controlled variable thermal gradient, for example, from a rim to a bore of a rotor. The thermal gradient can be linear, nonlinear, or both, and be applied or modified as the disk is rotating. The control system can maintain the thermal gradient and a rotational speed for a specified period of time. The control system also permits coordinated changes in rotational speed and disk temperature. For example, rotor temperature can be controlled using heating and cooling systems that are activated by the control system while rotational speed is being modulated. The control system also permits application of the thermal gradient and rotation induced mechanical loading for multiple TMF cycles or combined low cycle fatigue (LCF)/TMF cycles, for example. The test facility can implement tens of thousands of cycles that can be programmed to be similar for widely varying. In addition, the control system permits controllable and repeatable TMF loading conditions to be imposed on a number of test components, which can provide comparison data, as well as a set of standard or control conditions for experimental analysis.

Relatively high precision for control of quartz lamps is generally available, making the quartz lamp an attractive option as a heat source. The quartz lamps can be provided with a programmable power supply, which can be tied to a rotor speed control to create a speed-temperature ramp as desired. For example, a programmable logic controller (PLC) can be coupled to one or more quartz lamps and to a rotational speed controller to permit synchronized application of a thermal gradient with a particular rotational speed profile. The PLC can be used to control lamp on/off events, power levels or heat levels. For example, the PLC can have a feedback loop that controls and monitors lamp power or lamp heat output. With such an arrangement, the PLC can control a lamp to produce variable power or heat output. Operating profiles include, for example, operation at a given set point or producing a linear or nonlinear ramp over time. From a space and packaging standpoint, the quartz lamp system is also attractive for providing a low profile closely coupled heat source. The lamp control system may be used to implement set points that can be triggered to start other test sequence functions such as initiating and terminating cooling air flow and setting speed dwell times for rotor rotation.

The test facility may provide a test cycle that includes a number of stages. For example, a cycle may consist of the following portions: an ambient operating condition on a disk; a simultaneous increase in disk rotation speed and in disk temperature; establish and maintain a rim to bore or bore to rim thermal gradient; and applied cooling and reduced speed to ambient. Many other combinations or sequences are possible with the control system.

In addition, a sequence such as the one described above can be repeated for multiple cycles. Variations can also be introduced into the various cycles, such as by changing set points or other parameter values. For example, an applied temperature to create a thermal gradient can be increased, maintained or decreased across a number of cycles by controlling power supplied to a quartz lamp or by controlling heating times.

According to an exemplary sequence, a vacuum is drawn in the chamber of the test facility. During rotational acceleration, aerodynamic heating and loading can slow cycle times and shift expected thermal values. By evacuating the chamber during acceleration, desired rotational velocity can be achieved faster, with less impact of aerodynamic heating. During cool down, impingement air can be introduced to cool and slow the disk under test, potentially further shortening cycle times.

The above described testing uses the establishment of control strategies that integrate the rotational speed, vacuum, heating, dwell time and cooling sequences. Also, the test vehicle, data acquisition system (DAQ) and the test facility are operated in a manner that acquires the desired data in a safe and cost effective environment.

Various heating and cooling systems may be used in the test facility to establish a desired thermal gradient. Some examples are:

Impingement (convection) heating
Induction heating
Laser heating
Quartz heating lamps, alone and/or in a vacuum
Aerodynamic heating
Combinations of the above Some examples of cooling systems are chilled component cooling and impingement cooling.

Any other type of heating or cooling devices or techniques that can produce the desired gradients with the desired temperatures can be used. The heat source should be able to produce a desired temperature gradient on a test object spinning at a desired rate to achieve the objects of the disclosed system and method. Generated heat flux can be sufficiently coupled to the areas of interest on the test object to prevent stray radiation from heating features of the test object that are not pertinent to the desired testing. Insufficient heat flux coupling may reduce the efficiency of attaining a desired gradient. Sufficient and specific heat flux coupling can be achieved by, for example, using focused energy in tight annuli, employing heat rejection or complex cooling strategies. For example, thermal gradients can be generated from direct heating sources by shielding test component portions from direct heating sources to permit the portions to be indirectly heated. The test component may also be constructed to have limited component emissivity in part or in whole, such as by applying a coating to the test component, such as black high-temperature paint.

Regarding induction heating, in applications involving rotors with thin blades as the test object, the thermal energy applied to the disk rim also heats the blades. Heating thin sections, such as rear stage high-pressure compressor (HPC) blades, can represent risks, since the induced eddy currents that collect near free thin edges create overheating and local melting. Induction heating can be effective in heating large rotating structures with few changes in geometry such as semi-finished sonic shapes or material test samples.

Lasers used as localized heaters offer the ability to focus energy. However, the relatively high cost and sometimes limited availability of high power laser may have a practical impact on choosing such a heat source.

Quartz lamp technology has progressed over the years to the point where it has a high usage in manufacturing. Industrial processes such as heat treating and thermal curing have obtained significant benefits through quartz lamp heating. Power density can be relatively high with lamp elements running at temperatures as high as 4000° F. Polished, water cooled aluminum reflectors can be used to focus the energy from such lamps in narrow bands which can potentially duplicate the heating effect of a compressor flowpath.

Quartz halogen lamps can be effective in applications using rapid heating rates, precise control, and fast heat turn-on and turn-off times. A quartz lamp provides focused heat using a penetrating, short wave infrared output, which can heat directly into a depth of a test object, producing a more uniform heating of the object.

Quartz halogen lamps include a quartz envelope that can withstand relatively high temperatures. The filament of the lamp is larger compared to, for example, incandescent lamps, which can improve lamp life and increases the emitting area. The filament is helically wound tungsten, which is encased in the quartz envelope. Tungsten has a relatively fast response has a resistive element, and is capable of surviving temperatures in excess of 2750° C. The quartz envelope allows transmission of infrared energy, while protecting the filament from convective cooling and corrosion. The quartz is evacuated and filled with inert gases. A small amount of halogen gas is added to promote long life of the filament operating as an emitter. Rated life for most tungsten filament quartz lamps is about 5000 hours. Actual life typically depends upon the application and environment and may be greater of less than the rated life.

Quartz halogen lamp filaments are relatively small in comparison with the present heating application, which allows the output thermal energy to be optically focused toward a target. The lamps are available as linear emitters or point source emitters. Using a linear emitter and an elliptical reflector shape, the energy of the lamp can be redirected to a fine line. An ellipsoidal reflector can be used with a point source lamp to focus the energy to a point. A parabolic reflector generates parallel rays (rays that do not spread), resulting in narrow strips of heat. The reflector may be made of specular aluminum, ceramic, or other metals. The advantage of the aluminum reflector system is that it can be continually cooled and does not become a significant emitter of infrared. The aluminum is also polished to reflect and focus over 90% of the incident energy, for example.

Figure 18:
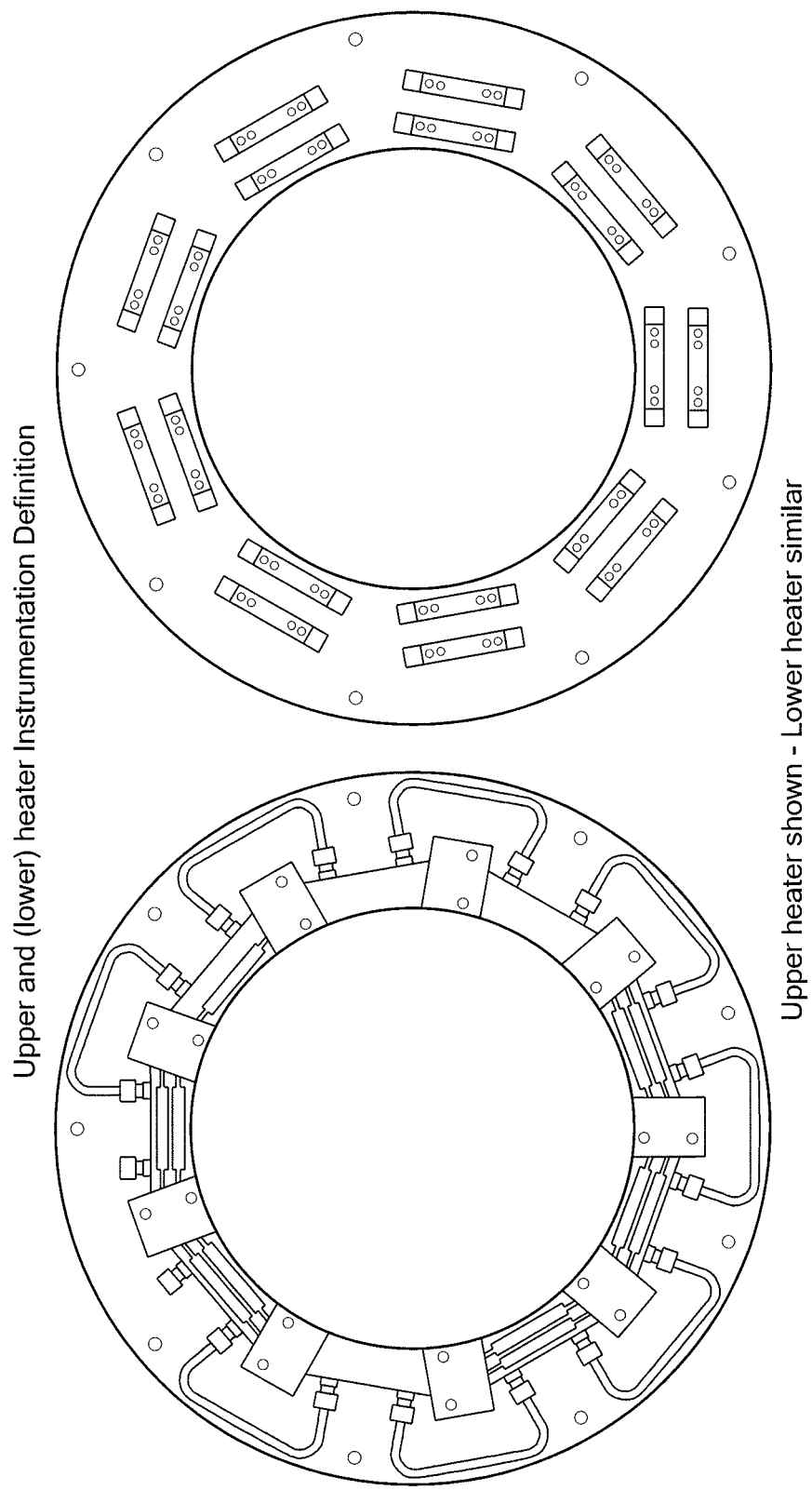
FIG. 18 is an illustration of a heater mechanism in accordance with an exemplary embodiment of the disclosed system and method.
Figure 19:
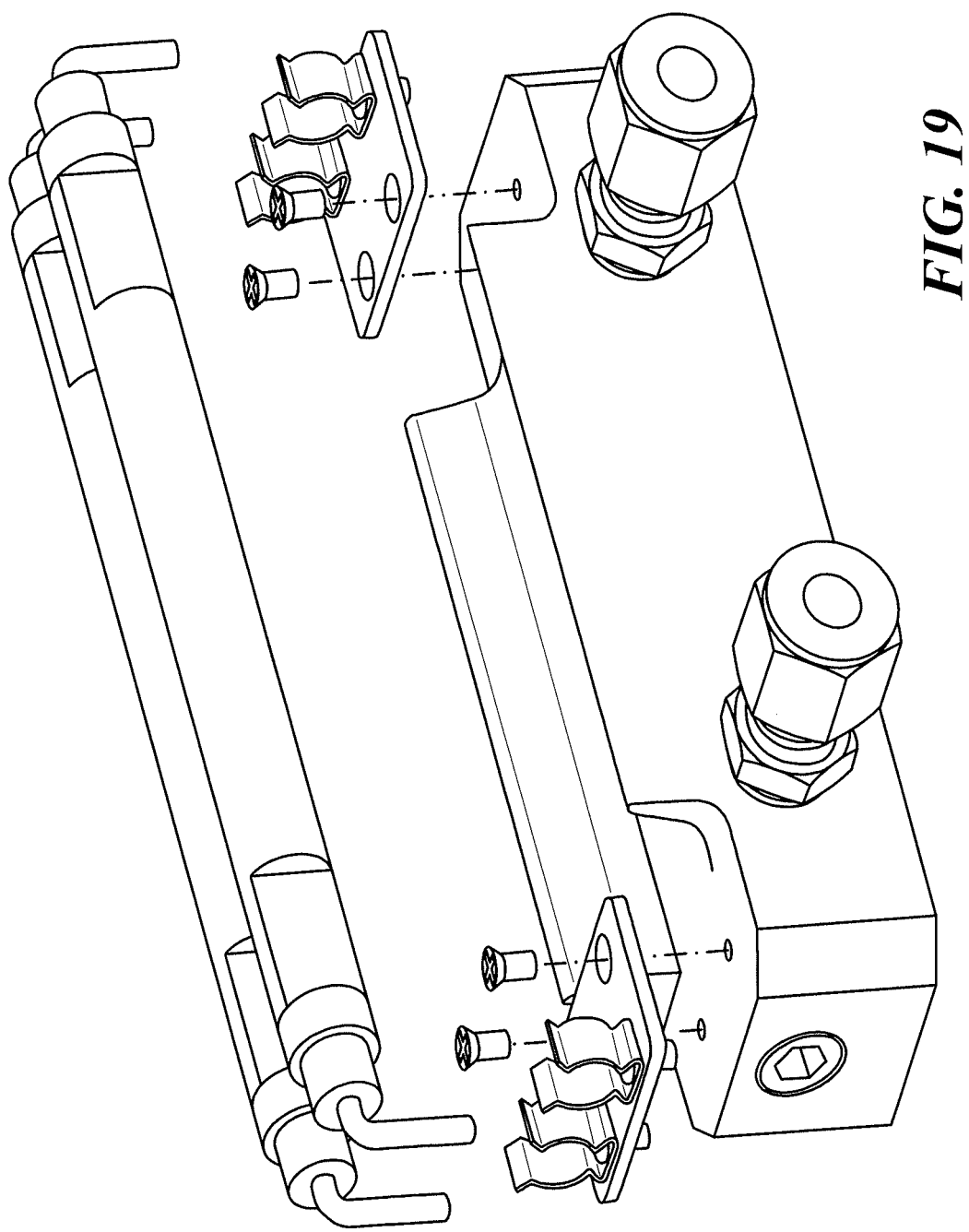
FIG. 19 is a perspective view of a quartz heater lamp in accordance with an exemplary embodiment of the disclosed system and method.

A quartz lamp with a chilled aluminum reflector permits non-contact heat transfer, which can be useful in applying heat to moving objects. Such a configuration is used in an embodiment of the disclosed test facility to obtain TMF loading on a rotor. FIG. 18 illustrates a quartz lamp heaters arranged in a disk or circular configuration for applying a high heat flux to one side at an outer edge of a test object. A correspondingly similar arrangement can be provided for applying a high heat flux to another side of the test object. FIG. 19 illustrates a quartz lamp configuration with retaining clips and a mounting structure The temperature and thermal gradients imposed on the test object are controlled by heating systems and controlled cooling provided by a cooling system. According to an embodiment of the present disclosure, an impingement cooling system is used for both controlling temperatures and thermal gradients, and for removing thermal gradients, for example. An effective impingement cooling system that may be used for cooling a disk rim and/or bore in the example case of a rotor as the test object may be specified based on various criteria. For example, the cooling system may be specified based on parameters such as cooling time desired, quantity and physical properties of impingement fluid, such as air, pressure, temperature and flow rate. The cooling system may be designed in part based on an estimate of the convective heat transfer coefficients (h). In addition, in the case of an impingement fluid, impingement nozzle orientation, location and quantity can be selectively chosen to achieve a desired cooling rate or parameter.

In a basic form, convective heat transfer can be represented by the following equation:

$$Q/A = h(To - Ta)$$

where:
Q/A=heat flux Btu/hr ft$^2$
h=Heat transfer coefficient Btu/hr ft$^2$° F.
Ta=temperature of the free stream ° F.
To=temperature at the wall ° F.

The mechanism of convective heat transfer is by conduction through a boundary layer. The exact value of h, and type of flow, i.e., forced, free, laminar or turbulent, determine the disk heat transfer and therefore the disk temperature versus time. An exact determination of the value of h is beyond the scope of the present disclosure and is not discussed here in detail. Various references, such as those incorporated into the present disclosure, provide a more in depth description of the methodology employed to determine the value of h.

The exemplary impingement cooling system is designed using the following parameters:
Total flow (Q)=1 lbm/sec shop air:
Assumption that both rim and bore impingement air is applied at the same time
Q rim max=0.7 lbm/sec directed @ rim
Q bore max=0.3 lbm/sec directed @ bore
70° F. available shop air
115 PSIA available shop air These parameters are used in the disk thermal analysis discussed above. The impingement air flow is treated as being uniformly distributed around the disk rim and bore. If the impingement air distribution is not uniform, h as used in the analysis may not be achieved, and cooling times may be longer than estimated.

In an exemplary embodiment, both sides of a rotor rim are impingement cooled. Such a configuration may help to avoid excessive thermal distortion of the rim, and may also minimize bending at the web. The impingement flow can be treated as choked flow through an orifice and can be determined by the following equation.

$$Q = CAP[G\,K\,M/RT]^{1/2}[2/(k+1)]^{[k+1/(2k-2)]}$$

where:
Q=flow rate (lbm/sec)
C=discharge coefficient=0.8
A=nozzle area (in$^2$)
P=pressure (PSIA)
G=386.04 (ft/sec$^2$)
K=specific heat ratio=1.4 (air)
M,R=universal gas constants
T=absolute temperature=520 (° R)

Assuming a uniform flow to each nozzle, and knowing the number of nozzles, the nozzle size can be determined. To minimize pressure drop in the system the upstream piping size is determined by maintaining an area ratio of 5-10:1, which minimizes upstream flow velocities. A similar approach is used to determine the bore impingement piping design. An additional design parameter is the orientation of the nozzle relative to the disk.

To maximize the impingement effect, the nozzle is oriented so that the impingement flow strikes the rotating disk at an angle. The angled impingement flow, in conjunction with the rotating disk surface, results in an effective impingement flow that is normal to the disk surface. Knowing the disk rotational speed, for example, 12,000 RPM, and impingement jet velocity, the relative angle can be determined.

During a portion of the test cycle when the impingement cooling is applied, the rotor rotational speed may, due to air drag on the rotor and the blade induced turbulence, be reduced by several thousand RPM. Impingement nozzles can be provided in a fixed orientation that is configured for average rotor speed operations. Other impingement cooling arrangements can be made that are dynamic or speed dependent. In the case of fixed nozzle orientation, the impingement cooling may be less effective for certain speed ranges. Other cooling provisions can be made to provide additional cooling at desired speed ranges if desired. For example, a cooling gas such as nitrogen or chilled air may be selectively employed with the impingement nozzles.

As an optional implementation, the quartz lamp retaining clips and electrical connections may be provided with heat shields to protect them from both air turbulence and radiant heat.

The arrangement of the spin test rig may prompt certain considerations for implementing cooling and temperature measurements for a given test object. For example, access to the cooling manifolds of the arbor may be limited. In such an instance, two (2) bore nozzles can be fit into the bore sub chamber to ensure adequate cooling capacity. The arbor, which is a heavy press fit into the disk bore, prevents access to the bore upper cavity, and may reduce disk bore impingement cooling to one side.

Figure 20:
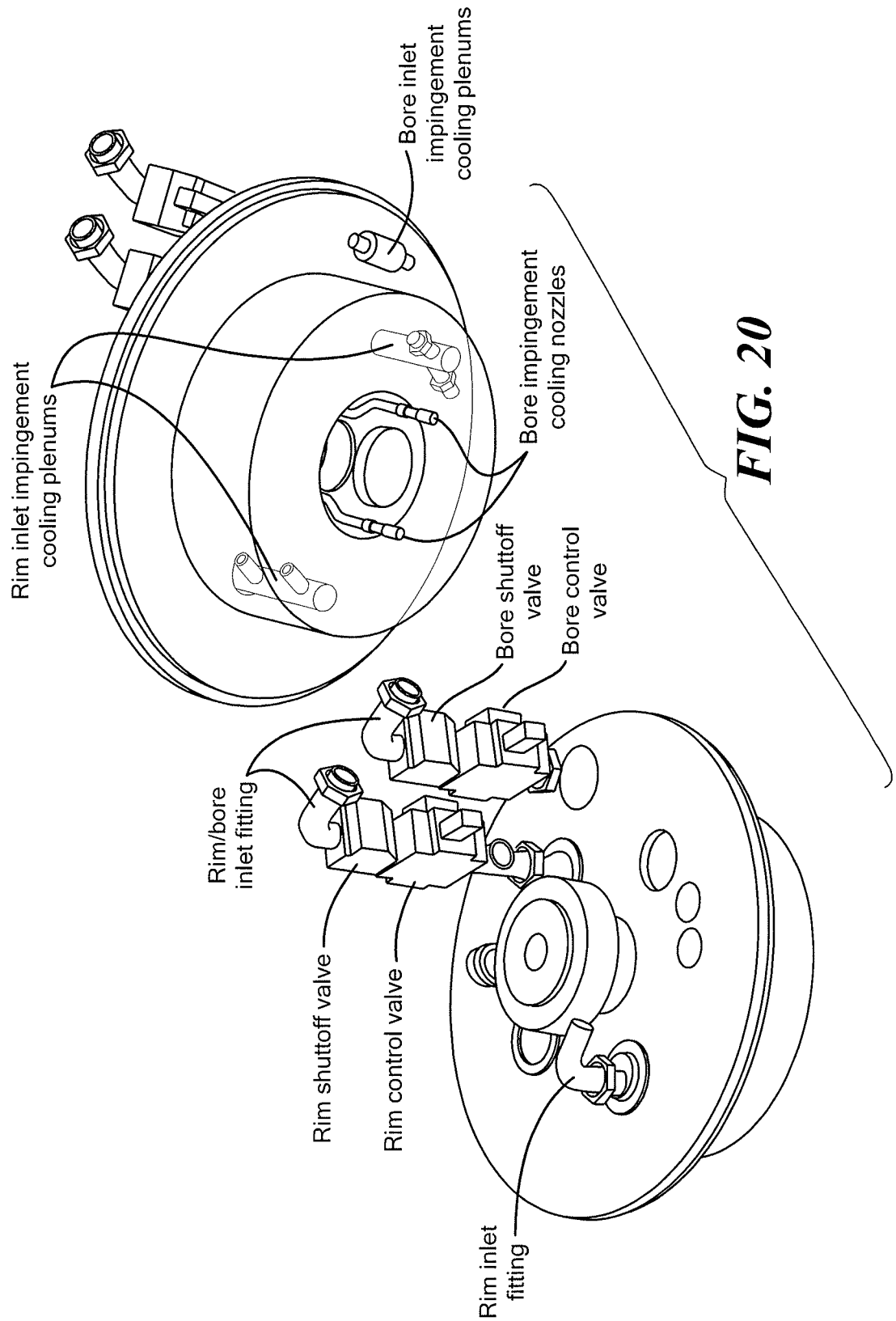
FIG. 20-22 are illustrations of cooling mechanisms applied in the test facility in accordance with an exemplary embodiment of the disclosed system and method.
Figure 21:
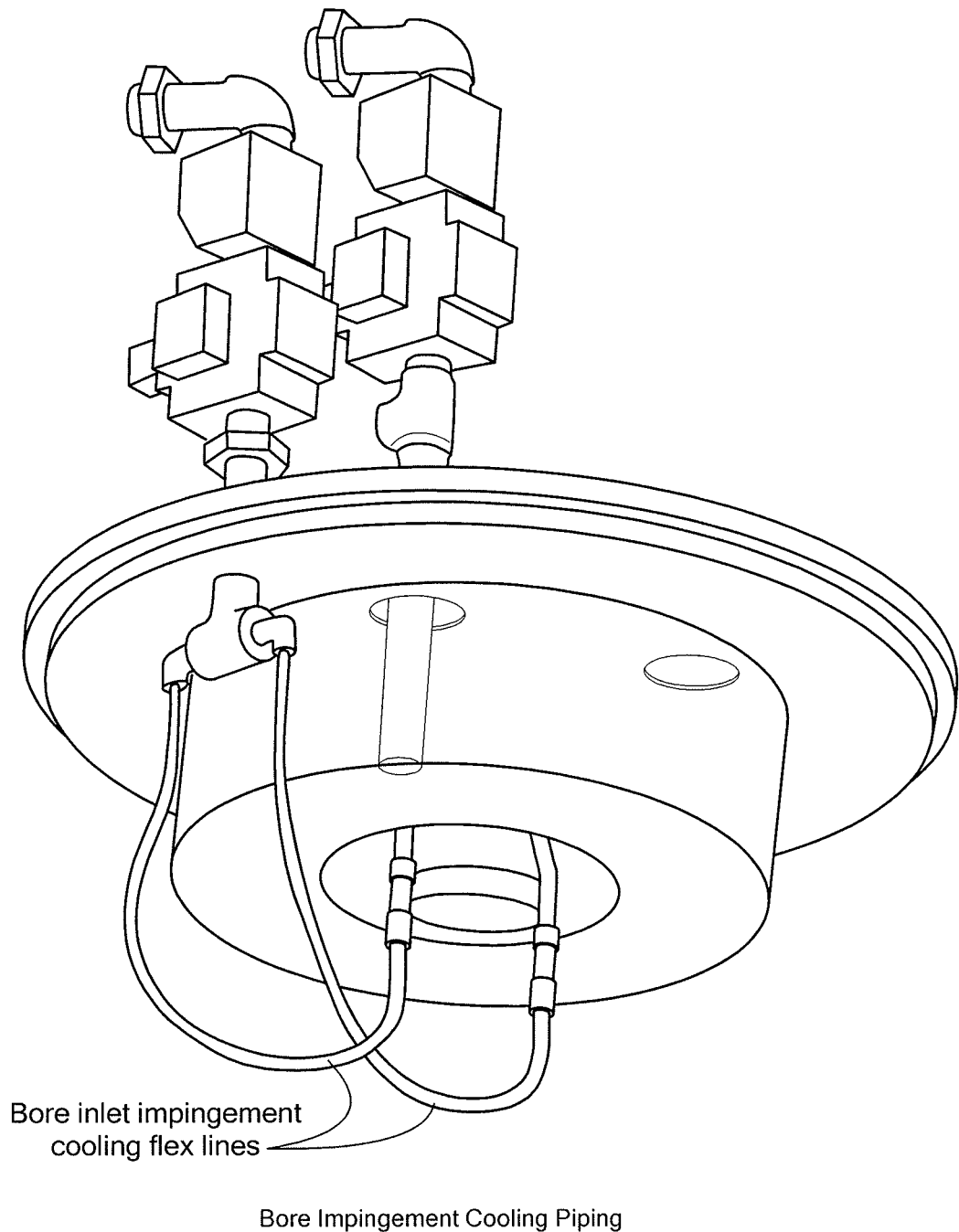
Figure 22:
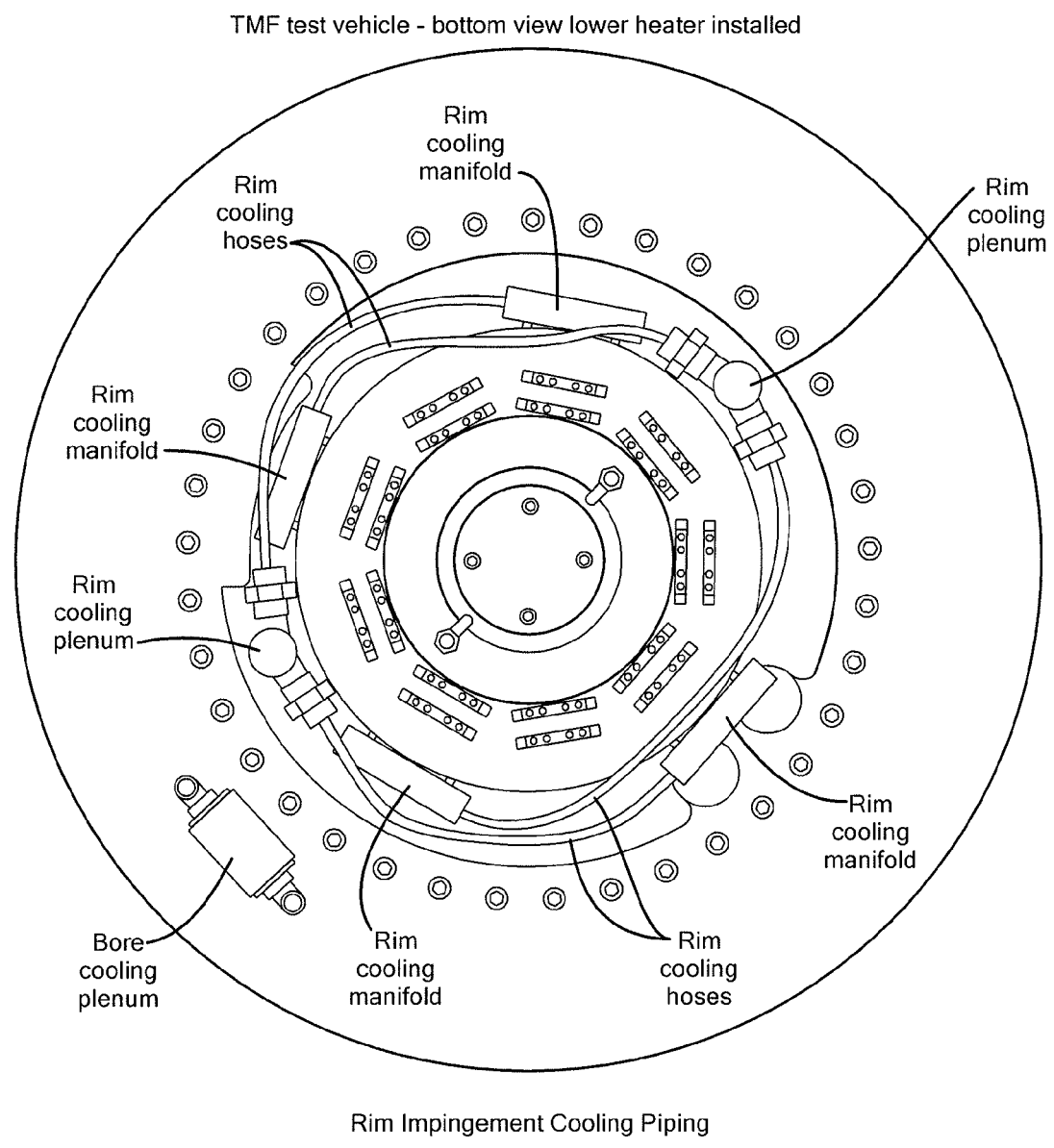

According to an exemplary embodiment, 16 rim nozzles are arranged in the test facility, with 8 directed at each side of the disk, in which rim nozzle diameter is 0.194 in and rim nozzle area is 0.0296 in$^2$. In addition, two nozzles are arranged in the bore, with a bore nozzle diameter equal to 0.2998 in and a bore nozzle area equal to 0.07059 in$^2$. The complete system arrangement and sizing is shown in FIGS. 20-22

With limited rim impingement coverage, a max h value is estimated to be 75-100. In the case of an example rotor, implementation of a bore cooling system may include additional or more frequent monitoring of the critical buckling temperature.

Figure 23:
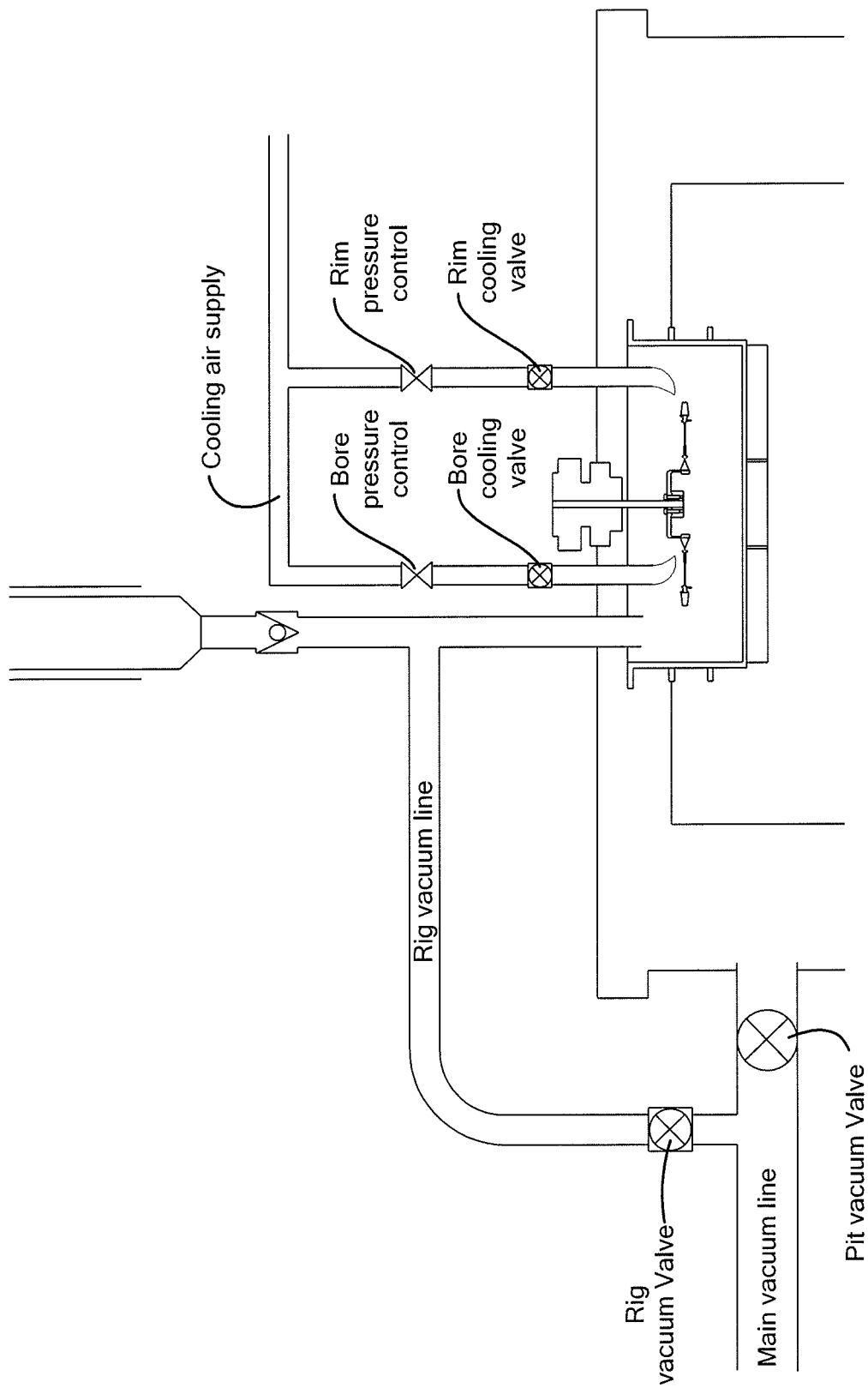
FIG. 23 is a valve diagram illustrating coolant flow paths in accordance with an exemplary embodiment of the disclosed system and method.

The use of impingement air for cooling may have other implications in the operation and response of the test facility. The drive motor for the test facility is turbine-based, meaning that a common air supply may be used to operate the motor drive as well as supply impingement cooling air. When impingement cooling air is applied to the test facility during rotational testing, a drive motor top speed may be reduced. Accordingly, the TMF cycle may impact the maximum RPM that the drive turbines can sustain. FIG. 23 shows a diagram of the facility and air system.

In addition, it is possible in some circumstances that aerodynamic heating can raise disk temperature during a cool down portion of a cycle. Prediction of these events and parameter values is complicated with a bladed rotor configuration. Other effects that may be quantified include airflow patterns into blades and pressure build up in the test chamber. In one embodiment, the drive motors, with 15 PSIA in the chamber, can maintain several thousand RPM. In an exemplary test, the drive motor was able to maintain 4500 RPM, and sub-chamber pressure can be set low enough such that aerodynamic heating does not create an issue with respect to disk buckling.

In an exemplary test in the test facility configured as discussed above, a rotor serves as the test component, which is an actual bladed high compressor rotor. The test facility is configured to apply a thermal gradient to the rotor using resistive heating elements. The predicted rim-to-bore thermal gradient is determined to be 450° F. using the above described analysis and modeling techniques. In practice, the actual thermal gradient achieved was 225° F. to 250° F. The rim temperature for the rotor under test reached a maximum of about 700° F. The actual thermal gradient produced during the test is less than the predicted thermal gradient obtained during the modeling and analysis phase. The reduced thermal gradient is due to radiant heat distribution in both the rim and the web of the rotor. The heat loss from the rim to the web of the rotor, coupled with the thermal emissivity of the web, indicates that a different test setup for the rotor testing may be implemented to obtain desired test conditions and results. The radiant heat distribution stems in part from the distance of the heat source from the test object and the lack of focused heat flux.

In addition, the modeling and analysis parameters can be updated to better correlate to actual test conditions. For example, the model used to predict the peak rim temperature of 1000° F. and gradient of 450° F. assumed that only a radial range of about 0.5 inches would be subjected to the heat flux, while no heat flux would be imposed on the web. By updating the model and analysis to reflect practical test conditions and alternate or additional heating and/or cooling sources, better predictions for a given test component can be obtained.

According to another exemplary test, the test facility is operated to verify the control system and test facility functionality. Vacuum, control, instrumentation calibration, safety system, over speed limiters, quartz heating, impingement cooling and quartz heater water cooling systems were all verified and calibrated. Control loops were tuned and control logic adjusted as desired. In addition, a controlled startup sequence was determined that permitted a full automatic control for the test facility. Prior to completing a full TMF test cycle, several "reduced" cycles were completed, with exemplary parameter values of 8000 RPM and 650° F. at the disk rim. The resulting data was analyzed and compared with expected data to verify test facility operation. At the completion of this testing the test facility was made available for the TMF testing. As a result of the initial test facility operation, a number of observations based on the empirical data that was collected were made.

For example, it was observed that the impingement cooling system is more effective that predicted. Impingement cooling flows of about 1 lb/sec were observed, which matched predictions. The turbine drive was also observed as being capable of maintaining 4500 RPM with impingement cooling air at maximum drive air flow rate. The quartz heaters performed as predicted and the disk speed control was observed to operate satisfactorily. The initial testing further showed that a disk thermal gradient can be controllable and repeatable.

Figure 24:
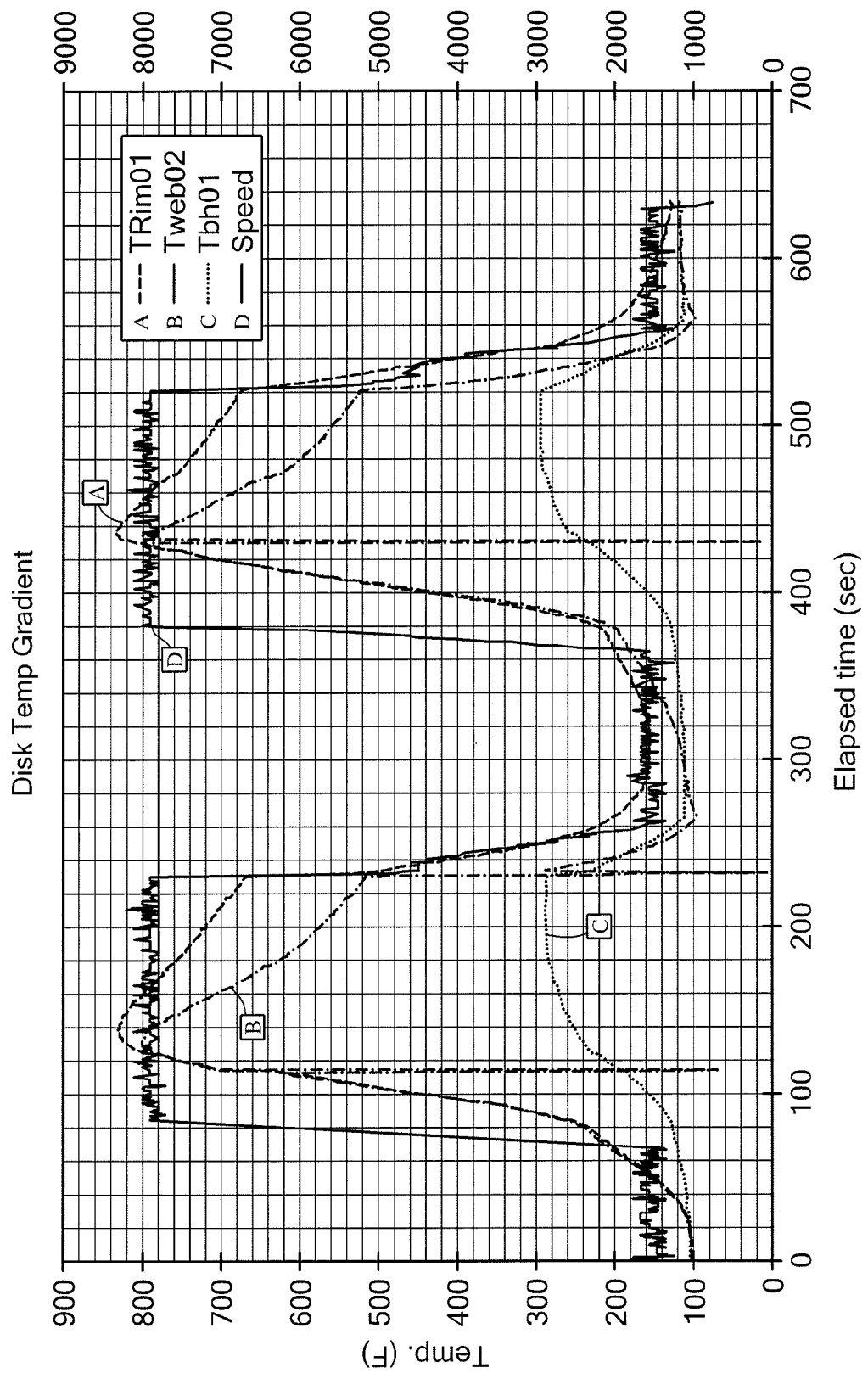
FIG. 24 is a graph illustrating rotor temperature gradients over time.

FIG. 24 shows TMF test cycle data for the above exemplary operation of the testing facility. The chart of FIG. 24 shows operational parameters while the control system is on full automatic. The temperature control loop is shown as being tuned during the test. The facility air and vacuum systems are cycled by the control system. Disk speed and temperature are cycled, and critical disk buckling temperature is being monitored by rim and bolt hole thermocouples.

According to another test example, a TMF test according to the disclosed system and method can be run using quartz heaters to establish and maintain a disk temperature profile, such as a rim-to-bore temperature gradient. The effectiveness of the heating source can be important in determining time, and power used, to heat the disk from ambient to maximum desired temperature. The quartz heaters can be employed to establish a thermal gradient in a vacuum being pulled in the test chamber to reduce mechanical loading on an accelerating rotor. The quartz heaters can radiantly heating the rim, which heat is conducted from the rim through the web into the bore.

From the previous modeling analysis, as indicated in FIG. 5, a lamp power of 20 kW is expected to provide a desired peak temperature. This power level is well within the capability of the quartz heating system, which may have maximum power level of 36 kW.

During actual testing the heat lamps may be modulated to reach and maintain a temperature as desired. Therefore, actual lamp power is not necessarily constant. Instrumentation such as thermocouples may be provided to read lamp power. Rim temperature/time readings can be taken during testing to determine correlation with the predictions illustrated in FIG. 5, and rim temperature gain predictions illustrated in FIG. 4.

A TMF testing cycle for the example rotor may be defined as follows:
Operating RPM: 1200<=RPM<=12000
Ambient temperature=300° F.
Max rim temperature=950° F.
Max bore temperature=450° F.
Dwell time @ Max Rim temperature/RPM=~100 sec
Cool down time 100-120 sec
Time to establish ambient temperature=60 sec
5 sec delay between disk acceleration and heat initiation
Total cycle time ~225 sec
Min RPM with cooling air on: 4000-8000

Figure 16:
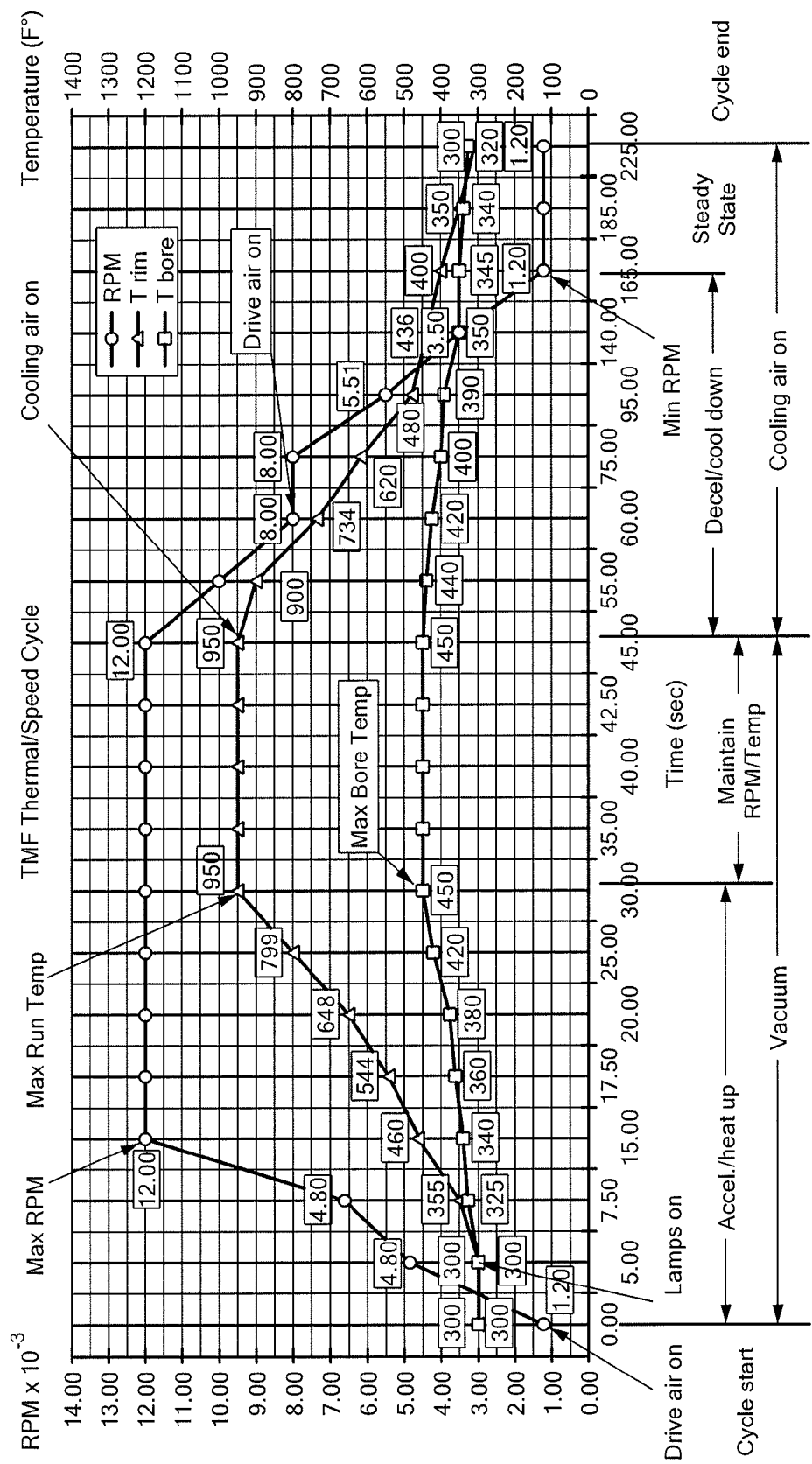
FIG. 16 is a graph illustrating parameters for a test cycle of a rotor in accordance with the disclosed system and method.

These parameters can be defined in the control system to implement a desired test cycling. A predicted cycle and test responses using these parameters is presented in FIG. 16.

Figure 25:
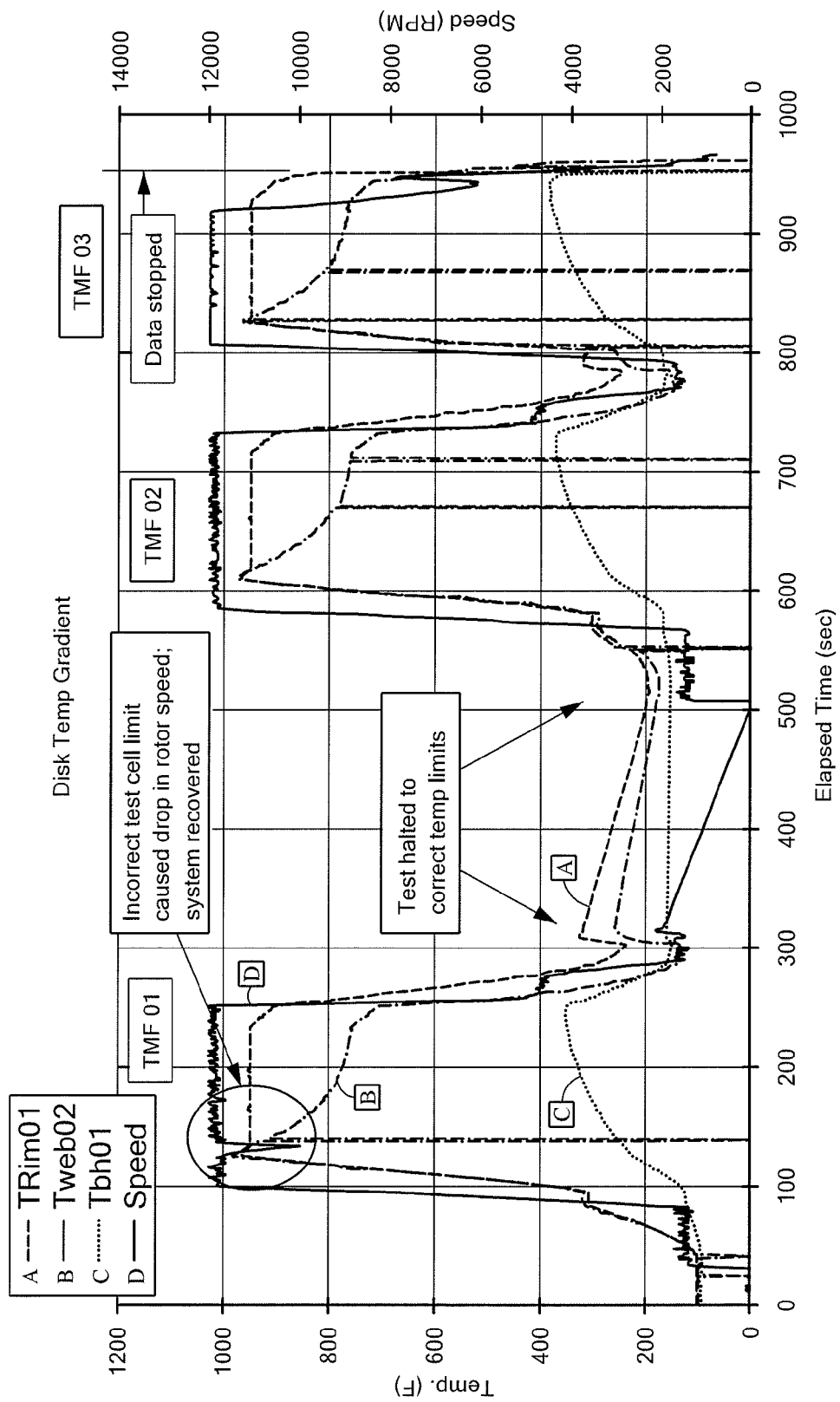
FIG. 25 is a graph illustrating rotor temperature gradients over time during a number of test cycles.
Figure 26:
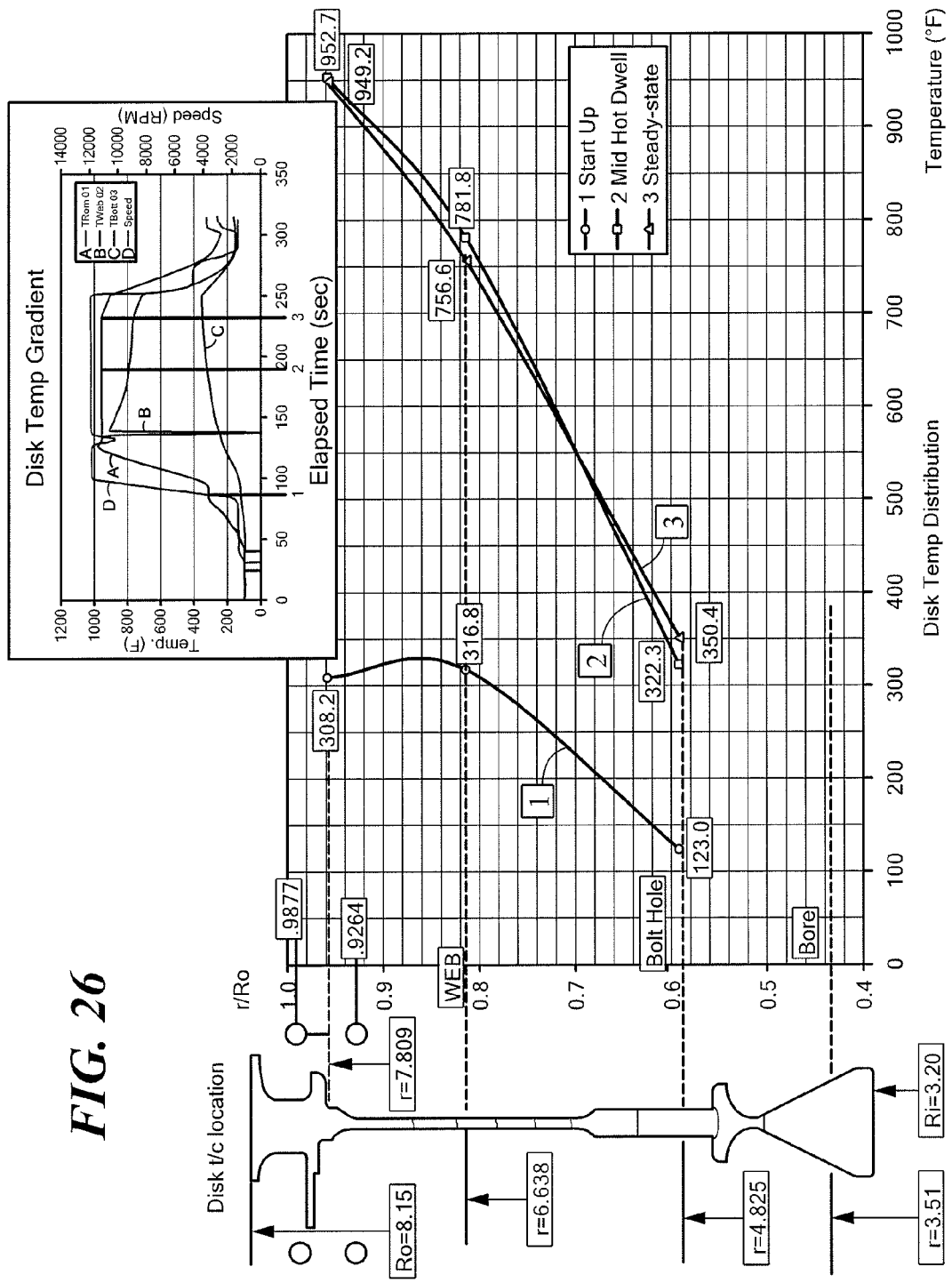
FIGS. 26-28 are graphs illustrating rotor temperature distribution during individual test cycles.
Figure 27:
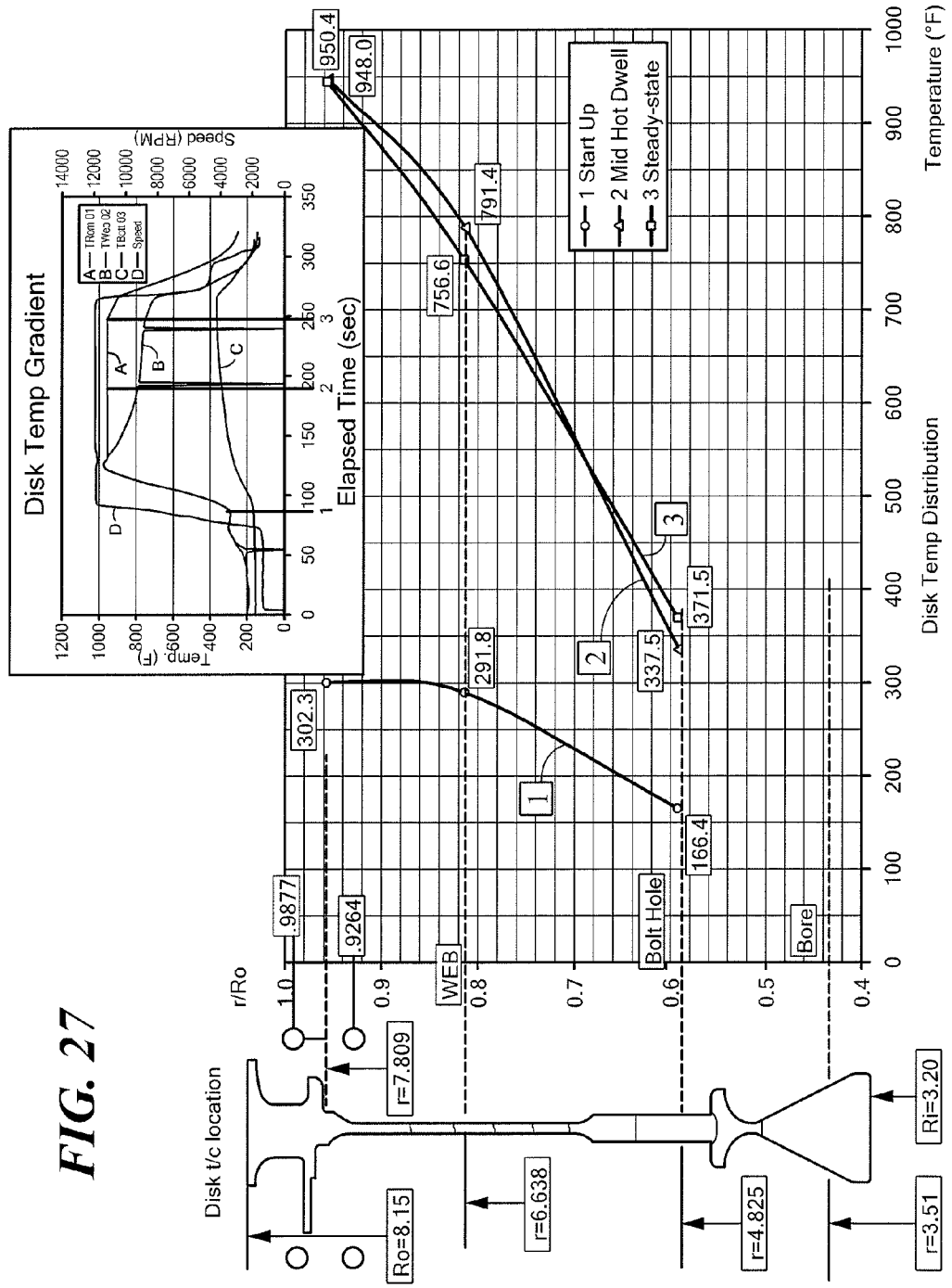
Figure 28:
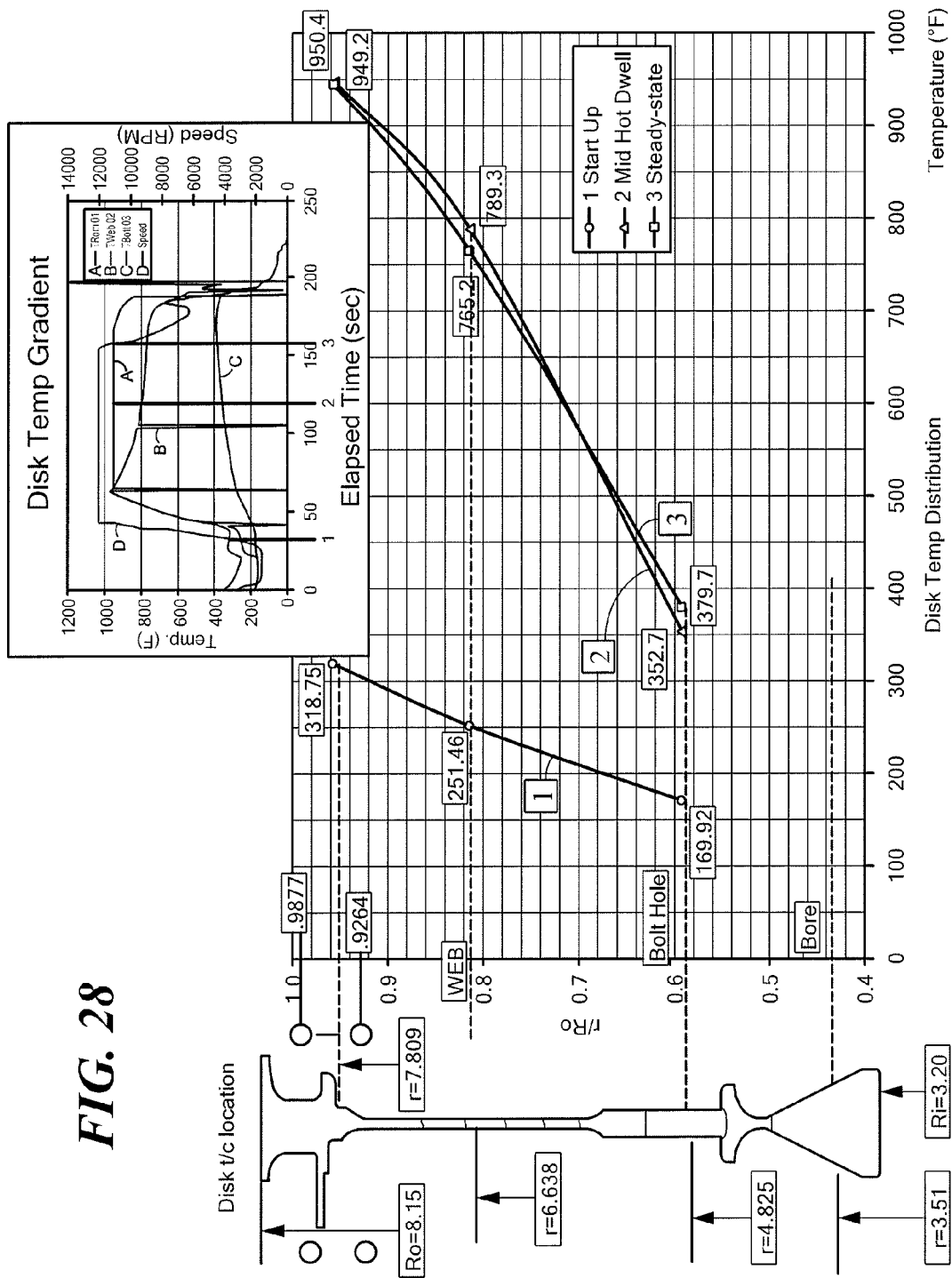

Four (4) TMF cycles were run using the above parameters in this exemplary embodiment, as illustrated in FIG. 25. The cycles are designated as TMF00, TMF01, TMF02 and TMF03. The time is interval between the end of TMF01 and the start of TMF02 represents a parameter set point change, as is permitted with the control system configuration.

As presented below in greater detail, TMF testing results with the impingement cooling system exceed expectations, and showed more rapid cooling times than anticipated. As is shown in the FIGS. 25-28, test objectives were satisfactorily achieved. For example, a repeatable disk temperature gradient of Trim=950° F., Tbore=350-370° F. was established. The temperature gradient and disk RPM were simultaneously cycled. It was observed that bolt hole temperature "creeps" over time, with Tbh in cycle TMF01=342° F. and Tbh in cycle TMF03=381° F.

The quartz heating system operated as intended, and the control system operated properly. The rim and bore impingement cooling systems were observed to operate effectively. The overall cycle time of ~220 sec is within planned test time. The disk was repeatedly cycled in both temperature and speed. Also, during testing, several data items were observed, including disk bore temperature, which was ~100° F. cooler that anticipated. As a comparison, 123° F. <=T bore test <=371° F. vs 300° F.<=T bore est <=450° F. This difference in bore temperature from predicted may be attributed to the presence of the disk arbor, which was not included in the initial modeling analysis.

Hot dwell time for the cycles can be controlled by modifying control system parameters, such as by changing set point values used for controlling the hot dwell time interval or by changing lamp power. During the test cycling, it was observed that a uniform disk temperature profile at idle (1200 PRM) was not re-established. This result is attributed to the arbor acting as a heat sink.

Test cycling showed that rim and web temperature profiles can be and were re-established. The impingement cooling times of the test cycles were less than anticipated measuring 52 sec versus 120 sec predicted. The difference in cooling time is attributed to higher convective heat transfer coefficients.

Radiant heating times for the disk rim were found to agree well with pre-test predictions. Analysis estimates for lamp power of 20 kW indicated a 30 sec heat up time, with temperatures starting at ambient (300° F.) and with a temperature gain of 21.847° F./sec. The test data is presented in Table 2 and 3 below, which shows good agreement with the estimate.

TABLE 2

|  | TMF00 | TMF01 | TMF02 | TMF03 |
|---|---|---|---|---|
| Start Time | 118.400 | 95.360 | 78.720 | 37.760 |
| Start Temp | 315.067 | 311.719 | 300.998 | 314.060 |
| Finish Time | 145.280 | 127.360 | 106.880 | 62.720 |
| Finish temp | 956.918 | 966.797 | 968.129 | 964.380 |

TABLE 3

| Cycle | Δtime Sec | $\Delta T_{rim}$ F. ° | Gain F. °/sec |
|---|---|---|---|
| TMF00 | 26.880 | 641.851 | 23.878 |
| TMF01 | 32.000 | 655.078 | 20.471 |
| TMF02 | 28.160 | 667.131 | 23.691 |
| TMF03 | 24.960 | 650.320 | 26.054 |
| Average | 28.000 | 653.595 | 23.524 |

The testing showed that the impingement cooling was more effective than pretest predictions. During testing, impingement cooling times were ~30-50 sec versus pretest predictions of 100-120 sec. This result implies that the convective heat transfer coefficient (h) is significantly higher than estimated. An estimate of $200 \leq h \leq 250$ can be made based on the above observations.

As discussed in the above disk thermal analysis, the calculation of h is dependent on an understanding of the exact air flow conditions. During impingement cooling the disk rotational speed is changing, air flow is being modulated by the control system and the rotor blades cause recirculation and turbulence. Accordingly, an accurate estimate for the value of h can be difficult to obtain.

Figure 29:
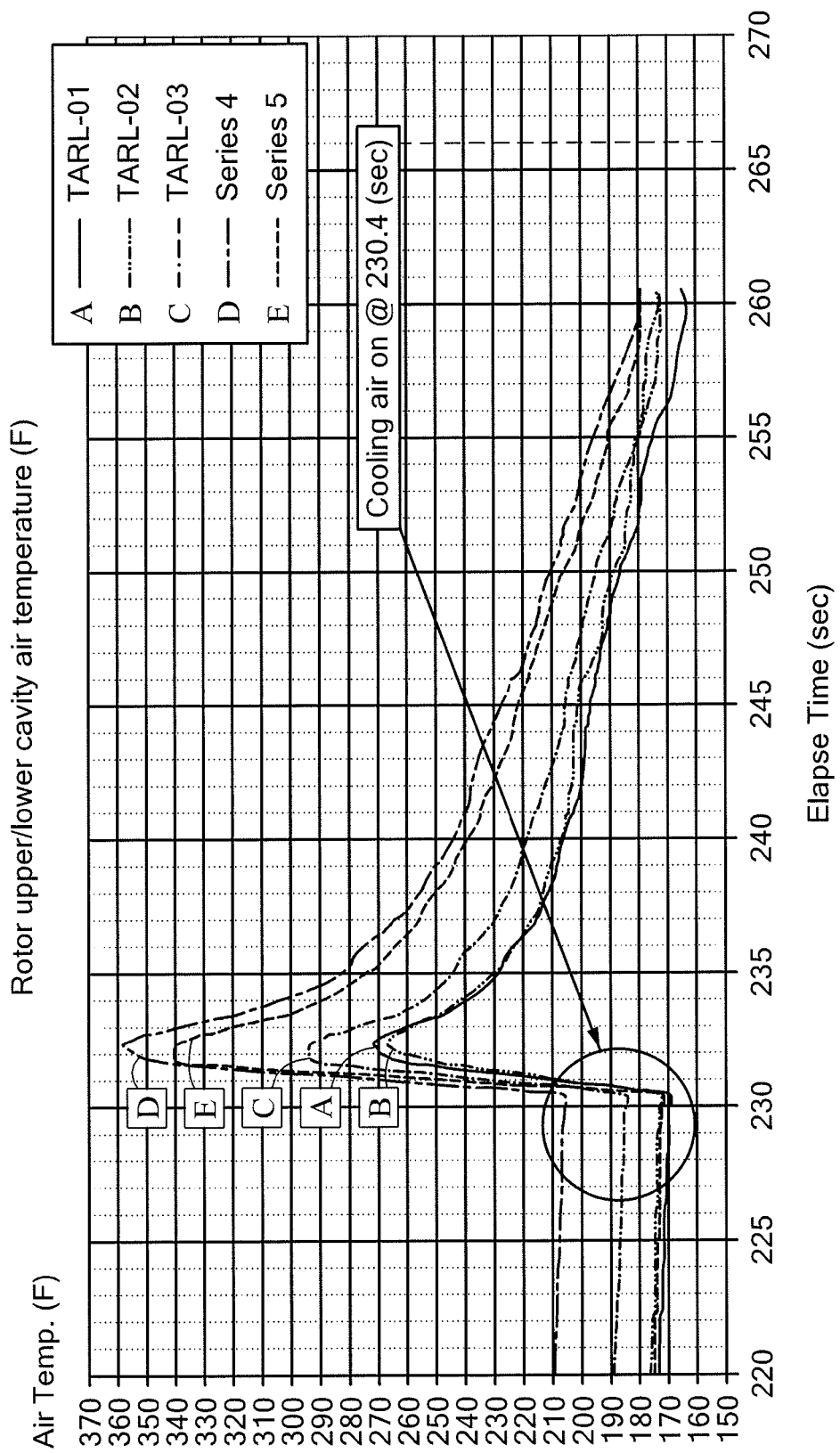
FIG. 29 is a graph illustrating rotor cavity air temperature.
Figure 30:
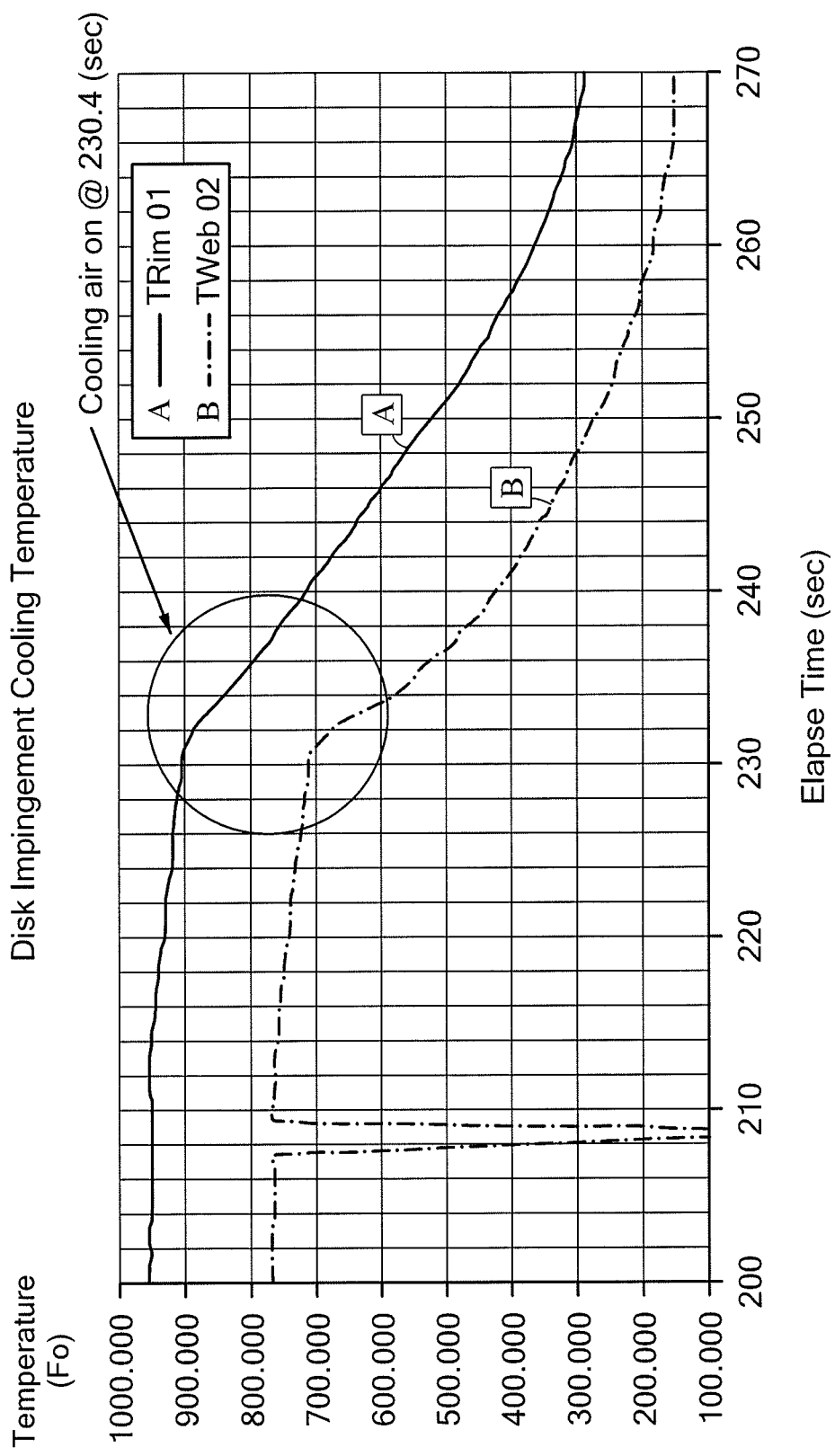
FIG. 30 is a graph illustrating rotor impingement cooling temperature.

Thermocouple readings taken from the rotor cavity, the area between the disk and the upper and lower heaters, show a large temperature rise that coincides with the initiation of impingement cooling air and the initial disk cool down, as illustrated in FIGS. 29-30 showing rotor cavity temperature change and disk cool down temperature.

The temperature rise noted in the rotor cavities is attributed to the heat pickup by the cooling air after flowing past the disk. At this point in the TMF cycle the radiant heaters are off, and the disk is the heat source in the system. The heat gained by the impingement air is the result of the convective heat transfer from the disk, and is about equal to the heat energy lost from the disk. However, balancing the heat energy gained in the air against the heat energy lost in the disk, due to convection, produces an unreasonably high value for h of greater than 1000. Such a value for h implies that there may be other unaccounted heat losses/gains.

In summary, the disclose test facility validated the possibilities for rapid and inexpensive TMF loading on test components such as a gas turbine engine compressor disk. The use of a quartz heating system as a radiant heat source allowed a controllable and repeatable disk temperature gradient to be established and maintained. Impingement cooling proved to be an effective method of quickly cooling the disk. The disk rotational speed was simultaneously cycled with disk heating and cooling and the cell functions were automatically controlled.

According to an exemplary embodiment, the test facility may be operated to obtain a clearer understanding of the air flow conditions during cooling, which may be used to completely define the disk thermal cycle. Pre-test predictions satisfactorily described the disk thermal and mechanical behavior.

Some applications for the test rig include those used to resolve fielded engine issues related to TMF or rim/lug region cracking, as well as advanced material development and testing programs where applying unique stresses on the disk is important. The development of the test rig may make it possible to induce unique stresses on select areas of the rotor, such as the rim, as well as the ability to tailor the bulk residual stresses in a rotor as part of the production spinning process. The test rig provides new and unique types of testing with numerous opportunities. For example, the test facility may help diagnose/test problems in the lug region, specifically stress rupture. The facility can induce unique and complex stress gradients for material and component testing. The test rig can also pre-stress the rim area of a rotor to test dual-microstructure disks or disks with bonded rims, for example.

Thermal gradients can be incorporated into production spins in accordance with the present disclosure to tailor location and magnitude of bulk residual stresses within the disk.

For example, possible TMF-related rotor failures may be analyzed with the disclosed system and method. The test rig constructed in accordance with the disclosed system and method can produce elevated temperature TMF cycles to replicate late stage compressor TMF. For example, rim temperatures near 1200-1300° F., with bore temperatures near 600-700° F. can be achieved, which can be extremely helpful for commercial engine applications.

Other exemplary test profiles possible with the test rig according to the disclosed system and method may include heating the bore area to put a pre-tensile load on the rim area, as well as creating steep radial gradients from rim to bore. For example, the test rig may be used for the development of a hybrid disk program that might explore options such as a dual microstructure disk, such as may include a finer grain at the bore for improved LCF life and courser grain near the rim for creep fatigue resistance. Other options that can be tested in the test rig include disks constructed by bonding different material rims, such as single-crystal nickel, onto a traditional nickel alloy disk.

Disk Thermal Spin Conditioning, such as is disclosed in U.S. Provisional Patent Application No. 61/021,002, filed Jan. 14, 2008, the entire contents of which are hereby incorporated herein by reference, as a spinning production process, is another exemplary application for the test rig in accordance with the disclosed system and method. Prior systems use a one-cycle production spin as part of the turbine rotor manufacturing process. These production spins distribute some of the bulk residual stresses that exist in the disk from the forging process, and help provide smooth LCF life margin in the bore. Some engine component manufacturers have also used elevated temperature proof spinning to further improve LCF margins, however these spins have only been conducted under isothermal conditions.

The test rig according to the disclosed system and method permits the development of production spinning under thermal gradient to further optimize and tailor the distribution of bulk residual stresses within the disk. There are a number of opportunities for employing such a concept. For example, the placement of bulk residuals can be tailored to combat rim stress rupture, TMF and creep fatigue. Bulk residuals can be tailored to improve fracture mechanics performance of disks. Bulk residual stresses from forging & manufacturing processes can be homogenized. Investigations of both lot-to-lot (same vendor) and vendor-to-vendor variability in the bulk residuals for turbine rotors can be assisted with the test facility according to the present disclosure. Variability can be substantial and may have fairly large effects on fatigue life performance of disks. Some of the variability is better understood and can be better controlled through the manufacturing process. The addition of a DTSC process may help homogenize and improve the distribution of the stresses, greatly reducing both known and unforeseen variability. The test facility can permit improved bore LCF performance in conjunction with dual heat treat microstructure disks.

The foregoing description is directed to particular embodiments of this invention. It will be apparent, however, that other variations and modifications may be made to the described embodiments, with the attainment of some or all of their advantages. Therefore, it is the object of the appended claims to cover all such variations and modifications as come within the true spirit and scope of the invention.

What is claimed is:

1. A system for inducing a coordinated thermal and mechanical load on a disk-shaped test object, comprising:
   a spin test rig suitable for mounting and rotating the test object about a central axis that is generally perpendicular to a plane of the disk of the test object to mechanically load the test object;
   a heat source being axially spaced from the test object at a radial position of the test object with respect to the axis, and arranged to output thermal energy in an axial direction to permit the output to be thermally coupled to a radial portion of the test object such that thermal energy can be applied from the heat source to the radial portion while the test object is rotating about the axis, to permit a radial thermal gradient to be established and maintained on the test object from the radial position of the heat source to another radial position on the test object; and
   a controller communicatively coupled to the spin test rig and the heat source to control the spin test rig to rotate the test object and to control the heat source to establish and maintain the radial thermal gradient while the test object is being rotated to permit the application of selectively synchronized thermal and mechanical loads to the test object.

2. The system according to claim 1, wherein the test object comprises a gas turbine engine rotor.

3. The system according to claim 1, further comprising a cooling source with an output being thermally coupled to the test object to cool the test object.

4. The system according to claim 3, wherein the cooling source further comprises an impingement cooling source that is operable to provide impingement cooling fluid to the test object.

5. The system according to claim 1, wherein the spin test rig further comprises a selectively sealable chamber for housing the test object.

6. The system according to claim 5, further comprising a vacuum source coupled to the chamber for evacuating chamber atmosphere.

7. The system according to claim 1, wherein the heat source comprises a radiant heat source.

8. The system according to claim 7, wherein the radiant heat source is a quartz lamp.

9. The system according to claim 8, further comprising a reflector located adjacent the quartz lamp to permit the applied thermal energy from the quartz lamp to be focused on the radial portion.

10. The system according to claim 9, further comprising a chilling source with an output being thermally coupled to the reflector to chill the reflector.

11. The system according to claim 1, wherein the controller is operable to provide signals to the spin test rig to rotate the test object at variable speeds, and is further operable to provide signals to the heat source to control the heat source to provide a variable amount of thermal energy to the radial portion of the test object while the test object is being rotated to permit application and removal of selectively synchronized thermal and mechanical loads on the test object in a cycle period for a plurality of consecutive cycle periods.

12. The system according to claim 11, further comprising the controller being communicatively coupled to a cooling source that includes an output that is thermally coupled to another radial portion of the test object to cool the test object, the controller being operable to provide signals to the cooling source to control the cooling source to provide a variable amount of cooling to the another radial portion of the test object while the test object is being rotated.

13. The system according to claim 11, further comprising the controller being operable to provide signals to the spin test rig and the heat source to obtain a specified phase difference between the thermal and mechanical loads.

14. A method for inducing a coordinated thermal and mechanical load on a disk-shaped test object, comprising:
   controlling a spin test rig to rotate the test object about a central axis that is generally perpendicular to a plane of the disk to mechanically load the test object;
   controlling a heat source that is axially spaced from the test object at a radial position of the test object to apply thermal energy in an axial direction to a radial portion of the rotating test object to establish and maintain a radial thermal gradient on the rotating test object to thermally load the test object; and coordinating the control of the spin test rig and the heat source to apply selectively synchronized thermal and mechanical loads to the test object.

15. The method according to claim 14, further comprising drawing a vacuum around the test object.

16. The method according to claim 14, further comprising extracting thermal energy from the test object.

17. The method according to claim 16, further comprising extracting thermal energy from the test object with impingement cooling.

18. The method according to claim 14, further comprising applying the thermal energy to the portion with a radiant heat source.

19. The method according to claim 18, further comprising employing a quartz lamp as the radiant heat source.

20. The method according to claim 19, further comprising focusing the applied thermal energy from the quartz lamp on the portion.

21. The method according to claim 14, further comprising rotating the test object with a variable speed in coordination with applying a variable thermal energy to the test object with the heat source.

22. The method according to claim 21, further comprising cooling the test object in coordination with rotating the test object with the variable speed.

23. The method according to claim 21, further comprising obtaining a specified phase difference between the thermal gradient and the mechanical load.

24. A method for testing a test object, comprising:

controlling a spin test rig to increase and decrease rotation of the test object mounted to the spin test rig to induce a mechanical load on the test object in a test cycle;

controlling a heat source thermally coupled to the test object to increase and decrease heat applied to the rotating test object at a radial distance from an axis of rotation to establish and remove a radial thermal gradient on the test object to induce a thermal load on the test object in the test cycle; and controlling the spin test rig and the heat source to coordinate the mechanical and thermal loads induced on the test object to have a predetermined phase difference in each of a number of consecutive test cycles.

* * * * *